(12) United States Patent
Chung

(10) Patent No.: US 10,357,549 B2
(45) Date of Patent: Jul. 23, 2019

(54) PIGMENT EPITHELIUM-DERIVED FACTOR (PEDF) AND PEPTIDE DERIVATIVES THEREOF FOR USE IN OSTEOBLAST DIFFERENTIATION AND BONE GROWTH

(71) Applicant: Yale University, New Haven, CT (US)

(72) Inventor: Chuhan Chung, Bethany, CT (US)

(73) Assignee: YALE UNIVERSITY, New Haven, CT (US)

( * ) Notice: Subject to any disclaimer, the term of this patent is extended or adjusted under 35 U.S.C. 154(b) by 34 days.

(21) Appl. No.: 15/328,147

(22) PCT Filed: Jul. 23, 2015

(86) PCT No.: PCT/US2015/041719
§ 371 (c)(1),
(2) Date: Jan. 23, 2017

(87) PCT Pub. No.: WO2016/014786
PCT Pub. Date: Jan. 28, 2016

(65) Prior Publication Data
US 2017/0216416 A1  Aug. 3, 2017

Related U.S. Application Data

(60) Provisional application No. 62/028,478, filed on Jul. 24, 2014.

(51) Int. Cl.
| | |
|---|---|
| *A61K 38/18* | (2006.01) |
| *C12N 5/077* | (2010.01) |
| *A61K 38/57* | (2006.01) |
| *A61K 38/55* | (2006.01) |
| *A61K 9/00* | (2006.01) |

(52) U.S. Cl.
CPC ............ *A61K 38/57* (2013.01); *A61K 9/0019* (2013.01); *A61K 38/18* (2013.01); *A61K 38/55* (2013.01); *C12N 5/0654* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 9,777,048 B2 | 10/2017 | Tsao et al. | |
| 2009/0069241 A1* | 3/2009 | Barnstable | C07K 14/811 514/13.3 |
| 2009/0202660 A1* | 8/2009 | Parhami | A61K 31/56 424/676 |
| 2010/0047214 A1 | 2/2010 | Abramson et al. | |
| 2010/0150880 A1 | 6/2010 | Aubin et al. | |
| 2013/0040899 A1* | 2/2013 | Shih | A61K 38/55 514/21.3 |

FOREIGN PATENT DOCUMENTS

| | | |
|---|---|---|
| WO | 2007095350 A2 | 8/2007 |
| WO | 2014043871 A1 | 3/2014 |

OTHER PUBLICATIONS

Longeras et al., Exp Diabetes Res. 2012;2012:518426.*
Li et al., Stem Cells. Dec. 2013;31(12):2714-2723.*
Goodman, PLOS Currents Huntington Disease. Feb. 25, 2011. Edition 1. doi: 10.1371/currents.RRN1214.*
Filleur et al., Cancer Res. Jun. 15, 2005;65(12):5144-5152 (Year: 2005).*
Bacerra et al., Nat Rev Cancer. Apr. 2013 ; 13(4): 258-271 (Year: 2013).*
Mirochnik et al., Clin Cancer Res. Mar. 1, 2009;15(5):1655-1663 (Year: 2009).*
Ek et al., Orthop Res. Dec. 2007;25(12):1671-1680 (Year: 2007).*
Becker, et al. "Exome sequencing identifies truncating mutations in human SERPINF1 in autosomal-recessive osteogenesis imperfecta," The American Journal of Human Genetics, 88:362-371, 2011.
Homan, et al., "Mutations in SERPINF1 cause osteogenesis imperfecta type VI," Journal of Bone and Mineral Research, 26(12):2798-2803, 2011.
Wang, et al., "Plasma pigment epithelium-derived factor is positively associated with obesity in Caucasian subjects, in particular with the visceral fat depot," European journal of endocrinology, 159:713-718, 2008.
Böhm, et al. "Common genetic variation in the SERPINF1 locus determines overall adiposity, obesity-related insulin resistance, and circulating leptin levels," PLoS One 7(3): e34035, 2012.
Ramírez-Castillejo, et al. "Pigment epithelium-derived factor is a niche signal for neural stem cell renewal," Nature neuroscience advance online publication, pp. 1-9, 2006.
Doyon, et al., "Nuclear receptor co-repressor is required to maintain proliferation of normal intestinal epithelial cells in culture and down-modulates the expression of pigment epithelium-derived factor," Journal of Biological Chemistry, 284(37):25220-25229, 2009.
Gonzalez, et al., "Screening the mammalian extracellular proteome for regulators of embryonic human stem cell pluripotency," Proceedings of the National Academy of Sciences, 107(8):3552-3557, 2010.
Kang, et al., "Proteomic characterization of the conditioned media produced by the visceral endoderm-like cell lines HepG2 and END2: toward a defined medium for the osteogenic/chondrogenic differentiation of embryonic stem cells," Stem cells and development, 18(1):77-92, 2009.

(Continued)

*Primary Examiner* — Daniel C Gamett
(74) *Attorney, Agent, or Firm* — Riverside Law LLP

(57) ABSTRACT

The present invention provides compositions and methods for differentiating a stem cell into an osteoblast or osteoblast progenitor cell. In certain embodiments, the invention may be used for promoting bone formation and increasing bone mass. In one embodiment, the composition comprises an agent which increases PEDF expression, PEDF activity, or both. In one embodiment, the composition comprises full-length PEDF. In one embodiment, the composition comprises a PEDF fragment or PEDF-derived peptide.

5 Claims, 16 Drawing Sheets
Specification includes a Sequence Listing.

(56) References Cited

OTHER PUBLICATIONS

Sabater, et al., "Circulating pigment epithelium-derived factor levels are associated with insulin resistance and decrease after weight loss," J Clin Endocrinol Metab, 95(10):4720-4728, 2010.
Wang, et al. "Pigment epithelium-derived factor suppresses adipogenesis via inhibition of the MAPK/ERK pathway in 3T3-L1 preadipocytes," American Journal of Physiology-Endocrinology and Metabolism, 297:E1378-E1387, 2009.
Chung, et al., "Anti-angiogenic pigment epithelium-derived factor regulates hepatocyte triglyceride content through adipose triglyceride lipase (ATGL)," Journal of Hepatology, 48:471-478, 2008.
Chung, et al., "Ethanol exposure depletes hepatic pigment epithelium-derived factor, a novel lipid regulator," Gastroenterology, 136:331-340, 2009.
Venturi, et al., "Lack of expression of SERPINF1, the gene coding for pigment epithelium-derived factor, causes progressively deforming osteogenesis imperfecta with normal type I collagen," Journal of Bone and Mineral Research 27(3):723-728, 2012.
Glorieux, et al., "Osteogenesis imperfecta type VI: a form of brittle bone disease with a mineralization defect," Journal of Bone and Mineral Research, 17(1): 30-38, 2002.
Bogan, et al. "A mouse model for human osteogenesis imperfecta type VI," Journal of Bone and Mineral Research 28(7):1531-1536, 2013.
Schmitz, et al. "Pigment epithelium-derived factor regulates early pancreatic fibrotic responses and suppresses the profibrotic cytokine thrombospondin-1," The American journal of pathology 179(6):2990-2999, 2011.
Grippo, et al., "Concurrent PEDF deficiency and Kras mutation induce invasive pancreatic cancer and adipose-rich stroma in mice," Gut 61:1454-1464, 2012.
Kratchmarova, et al., "A proteomic approach for identification of secreted proteins during the differentiation of 3T3-L1 preadipocytes to adipocytes," Molecular & Cellular Proteomics, 1:213-222, 2002.
Crowe, et al. "Pigment epithelium-derived factor contributes to insulin resistance in obesity," Cell metabolism 10:40-47, 2009.
Rodeheffer, et al., "Identification of white adipocyte progenitor cells in vivo," Cell, 135:240-249, 2008.
Doll, et al., "Pigment epithelium-derived factor regulates the vasculature and mass of the prostate and pancreas," Nature medicine, 9(6):774-780, 2003.
Yasui, et al. "Dual-site recognition of different extracellular matrix components by anti-angiogenic/neurotrophic serpin, PEDF," Biochemistry, 42:3160-3167, 2003.
Rauch, et al. "Lack of circulating pigment epithelium-derived factor is a marker of osteogenesis imperfecta type VI," The Journal of Clinical Endocrinology & Metabolism, 97:E1550-E1556, 2012.
Yamagishi, et al., "Elevated serum levels of pigment epithelium-derived factor in the metabolic syndrome," The Journal of Clinical Endocrinology & Metabolism, 91(6):2447-2450, 2006.
Matsumoto, et al. "Antiangiogenic property of pigment epithelium-derived factor in hepatocellular carcinoma." Hepatology 40:252-259, 2004.
Moreno-Navarrete, et al. "Liver, but not adipose tissue PEDF gene expression is associated with insulin resistance," International Journal of Obesity, 37:1230-1237, 2013.
Farber, et al., "A Novel IFITM5 Mutation in Severe Atypical Osteogenesis Imperfecta Type VI Impairs Osteoblast Production of Pigment Epithelium-Derived Factor," Journal of Bone and Mineral Research 29(6):1402-1411, 2014.
Gattu, et al., "Determination of mesenchymal stem cell fate by pigment epithelium-derived factor (PEDF) results in increased adiposity and reduced bone mineral content," The FASEB Journal 27:4384-4394, 2013.
Goodman, et al., "Body composition in premanifest Huntington's disease reveals lower bone density compared to controls," PLoS Currents Huntington Disease, 2011, http://currents.plos.org/hd/article/body-composition-in-premanifest-huntingtons-disease-reveals-lower-bone-density-compared-to-controls/.
Lecka-Czernik, et al. "Divergent effects of selective peroxisome proliferator-activated receptor-$\gamma$2 ligands on adipocyte versus osteoblast differentiation," Endocrinology, 143(6):2376-2384, 2002.
DuBose, et al. "Thrombospondin-1 inhibits osteogenic differentiation of human mesenchymal stem cells through latent TGF-$\beta$ activation," Biochemical and biophysical research communications, 422(3): 488-493, 2012.
Koli, et al., "Latent TGF-$\beta$ binding proteins (LTBPs)-1 and -3 coordinate proliferation and osteogenic differentiation of human mesenchymal stem cells," Bone, 43:679-688, 2008.
Krishnan, et al., "Regulation of bone mass by Wnt signaling," The Journal of clinical investigation, 116(5):1202-1209, 2006.
Park, et al., "Identification of a novel inhibitor of the canonical Wnt pathway," Molecular and cellular biology, 31(14):3038-3051, 2011.
Ross, et al., "Microarray analyses during adipogenesis: understanding the effects of Wnt signaling on adipogenesis and the roles of liver X receptor a in adipocyte metabolism," Molecular and cellular biology, 22(16):5989-5999, 2002.
Bradshaw, et al. "SPARC-null mice exhibit increased adiposity without significant differences in overall body weight," PNAS, 100(10): 6045-6050, 2003.
Nie, et al., "SPARC inhibits adipogenesis by its enhancement of $\beta$-catenin signaling," Journal of Biological Chemistry, 284(2):1279-1290, 2009.
Prockop, "New Targets for Osteoporosis," N Engl J Med, 367(24):2353-2354, 2012.

\* cited by examiner

1. DPFFKVPVNKLAAAVSNFGYDLYRVRSSTSPTTN (SEQ ID NO: 1)
2. DPFFKVPVNKIAAAVSNFGYDLYRVRSSTSPTTN (SEQ ID NO: 2)
3. DPFFKVPVNKEAAAVSNFGYDLYRVRSSTSPTTN (SEQ ID NO: 3)
4. DPFFKVPVNALAAAVSNFGYDLYRVRSSTSPTTN (SEQ ID NO: 4)
5. DPFFKVPVNAIKAAVSNFGYDLYRVRSSTSPTTNAIK (SEQ ID NO: 5)

hMSCs 7days in osteogenic media+/-100nM peptide

```
                        SEQUENCE LISTING

<160> NUMBER OF SEQ ID NOS: 11

<210> SEQ ID NO 1
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 1

Asp Pro Phe Phe Lys Val Pro Val Asn Lys Leu Ala Ala Ala Val Ser
1               5                   10                  15

Asn Phe Gly Tyr Asp Leu Tyr Arg Val Arg Ser Ser Thr Ser Pro Thr
            20                  25                  30

Thr Asn

<210> SEQ ID NO 2
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 2

Asp Pro Phe Phe Lys Val Pro Val Asn Lys Ile Ala Ala Ala Val Ser
1               5                   10                  15

Asn Phe Gly Tyr Asp Leu Tyr Arg Val Arg Ser Ser Thr Ser Pro Thr
            20                  25                  30

Thr Asn

<210> SEQ ID NO 3
<211> LENGTH: 34
<212> TYPE: PRT
<213> ORGANISM: Artificial Sequence
<220> FEATURE:
<223> OTHER INFORMATION: Chemically Synthesized

<400> SEQUENCE: 3

Asp Pro Phe Phe Lys Val Pro Val Asn Lys Glu Ala Ala Ala Val Ser
1               5                   10                  15

Asn Phe Gly Tyr Asp Leu Tyr Arg Val Arg Ser Ser Thr Ser Pro Thr
            20                  25                  30

Thr Asn

<210> SEQ ID NO 4
<211> LENGTH: 34
```

```
<212> TYPE: PRT
<213> ORGANISM: Artificial Sequence
<220> FEATURE:
<223> OTHER INFORMATION: Chemically Synthesized

<400> SEQUENCE: 4

Asp Pro Phe Phe Lys Val Pro Val Asn Ala Leu Ala Ala Ala Val Ser
1               5                   10                  15

Asn Phe Gly Tyr Asp Leu Tyr Arg Val Arg Ser Ser Thr Ser Pro Thr
            20                  25                  30

Thr Asn

<210> SEQ ID NO 5
<211> LENGTH: 37
<212> TYPE: PRT
<213> ORGANISM: Artificial Sequence
<220> FEATURE:
<223> OTHER INFORMATION: Chemically Synthesized

<400> SEQUENCE: 5

Asp Pro Phe Phe Lys Val Pro Val Asn Ala Ile Lys Ala Ala Val Ser
1               5                   10                  15

Asn Phe Gly Tyr Asp Leu Tyr Arg Val Arg Ser Ser Thr Ser Pro Thr
            20                  25                  30

Thr Asn Ala Ile Lys
        35

<210> SEQ ID NO 6
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 6
aagttctggg tcacggtcag                                               20

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
acgatacggc ttggactctg                                               20

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 8
gggcgtctat acccgagtgt                                               20

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
```

```
agccacgtgt ctctggtgtc                                              20

<210> SEQ ID NO 10
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 10
agggctttgt gacgggaaca g                                            21

<210> SEQ ID NO 11
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 11
ggcacccggt caaatgaga                                               19
```

PIGMENT EPITHELIUM-DERIVED FACTOR (PEDF) AND PEPTIDE DERIVATIVES THEREOF FOR USE IN OSTEOBLAST DIFFERENTIATION AND BONE GROWTH

CROSS-REFERENCE TO RELATED APPLICATIONS

This application is a U.S. national phase application filed under 35 U.S.C. § 371 claiming benefit to International Patent Application No. PCT/US2015/041719, filed Jul. 23, 2015, which is entitled to priority under 35 U.S.C. § 119(e) to U.S. Provisional Patent Application No. 62/028,478, filed Jul. 24, 2014, each of which application is hereby incorporated herein by reference in its entirety.

STATEMENT REGARDING FEDERALLY SPONSORED RESEARCH OR DEVELOPMENT

This invention was made with government support under AR046032 and DK034989 awarded by the National Institute of Health. The government has certain rights in the invention.

BACKGROUND OF THE INVENTION

The differentiation of stem cells into distinct tissues can be regulated by specific extracellular signaling molecules. For example, Wnt ligands and VEGF differentially regulate mesenchymal stem cell (MSC) fate into adipocytes or osteoblasts (Krishnan et al., 2006, J. Clin. Invest., 116: 1202-1209; Leck-Czernik et al., 2002, Endocrinology, 143: 2376-2384; Liu et al., 2012, J. Clin. Invest., 122: 3101-3113; Prockop et al., 2012, N. Engl. J. Med., 367: 2353-2354). Two human diseases affecting adipocytes and osteoblasts, obesity and osteogenesis imperfecta (OI) type VI, have been associated with an excess or complete absence of pigment epithelium-derived factor (PEDF) (Becker et al., 2011, Am. J. Hum. Genet., 88: 362-371; Homan et al., 2011, J. Bone Miner. Res., 26: 2798-2803; Wang et al., 2008, Eur. J. Endocrinol. 159: 713-718; Bohm et al., 2012, PLoS One, 7:e34035). PEDF is a 50-kDa secreted multifunctional protein of the SERPIN superfamily that has been implicated in the regulation of stem cell populations (Ramirez-Castillejo et al., 2006, Nat Neurosci, 9: 331-339; Doyon et al., 2009, J Biol Chem., 284: 25220-25229; Gonzalez et al., 2010, Proc Natl Acad Sci USA, 107:3552-3557; Kang et al., 2009, Stem Cells Dev, 18:77-91).

The clinical manifestations of high PEDF versus its absence point to its role in adipocyte and osteoblast development. Increased PEDF levels correlate with adiposity in patients with the metabolic syndrome (Wang et al., 2008, Eur. J. Endocrinol. 159: 713-718; Bohm et al., 2012, PLoS One, 7:e34035; Sabater et al., 2010, J Clin Endocrinol Metab, 95: 4720-4728). Here, elevated PEDF likely represents a compensatory measure since PEDF impedes adipogenesis of 3T3-L1 adipocyte precursors and its absence in mice results in ectopic lipid accumulation in organs such as the liver and pancreas (Wang et al., 2009, Am J Physiol Endocrinol Metab, 297: E1378-1387; Chung et al., 2008, J Hepatol, 48: 471-478; Chung et al., 2009, Gastroenterology, 136:331-340 e332). Conversely, individuals lacking PEDF because of null mutations have OI type VI, an autosomal recessive form of OI characterized clinically by fractures of bone due to inadequate mineralization (Homan et al., 2011, J. Bone Miner. Res., 26: 2798-2803; Venturi et al., 2012, J Bone Miner Res., 27: 723-728). Bone specimens from patients with OI type VI reveal severely hypomineralized bones that are mirrored in a mouse model of PEDF deficiency (Glorieux et al., 2002, J Bone Miner Res, 17: 30-38; Bogan et al., 2013, J Bone Miner Res., 28: 1531-1536). The mineralization defect was associated with abnormalities in the extracellular matrix that were reported in osteoblast cultures and bones from these mice (Bogan et al., 2013, J Bone Miner Res., 28: 1531-1536). Although exome sequencing established null mutations in the PEDF gene as the cause of OI type VI, a mechanism for the phenotype remains unclear (Becker et al., 2011, Am. J. Hum. Genet., 88: 362-371; Homan et al., 2011, J. Bone Miner. Res., 26: 2798-2803; Venturi et al., 2012, J Bone Miner Res., 27: 723-728).

It has been previously reported that there exists obvious abnormalities of mesenchymal progenitor-derived cells in the livers and pancreas of PEDF knockout (KO) mice (Chung et al., 2009, Gastroenterology, 136:331-340 e332; Schmitz et al., 2011, Am J Pathol, 179: 2990-2999). This included a striking pattern of a-smooth actin staining reflecting activation of mesenchymal progenitor-derived cells (Chung et al., 2009, Gastroenterology, 136:331-340 e332; Schmitz et al., 2011, Am J Pathol, 179: 2990-2999). Also prominent was the marked presence of lipid droplet markers in PEDF KO fibroblasts in organs normally devoid of adipocytes (Grippo et al., 2012, Gut, 61: 1454-146).

A prior study suggested that PEDF may induce osteoblast differentiation from embryonic stem cells, but PEDF dependency was not evaluated (Kang et al., 2009, Stem Cells Dev, 18:77-91). Whether PEDF plays a direct role in the commitment and differentiation of MSCs into adipocytes or osteoblasts, the two cell types underlying the extremes of PEDF-related human diseases, has not been investigated.

Thus, there is a need in the art for compositions and methods for modulating MSC differentiation. The present invention satisfies this unmet need.

SUMMARY OF THE INVENTION

The present invention provides a composition for differentiating a stem cell into the osteoblast lineage, wherein the composition comprises an agent that increases PEDF activity.

In one embodiment, the agent comprises an isolated peptide. In one embodiment, the agent comprises full-length PEDF. In one embodiment, the isolated peptide comprises a PEDF-derived peptide. In one embodiment, the PEDF-derived peptide comprises an amino acid sequenced selected from SEQ ID NOs: 1-5.

In one embodiment, the agent comprises an isolated nucleic acid. In one embodiment, the isolated nucleic acid encodes full-length PEDF. In one embodiment, the isolated nucleic acid encodes a PEDF-derived peptide. In one embodiment, the PEDF-derived peptide comprises an amino acid sequenced selected from SEQ ID NOs: 1-5.

The present invention provides a method of differentiating a stem cell into the osteoblast lineage, the method comprising culturing the stem cell in the presence of a composition comprising an agent that increases PEDF activity.

In one embodiment, the agent comprises an isolated peptide. In one embodiment, the agent comprises full-length PEDF. In one embodiment, the isolated peptide comprises a PEDF-derived peptide. In one embodiment, the PEDF-derived peptide comprises an amino acid sequenced selected from SEQ ID NOs: 1-5.

The present invention provides a method of treating or preventing a condition associated with reduced bone mass in a subject in need thereof, the method comprising administering to the subject an effective amount of a composition comprising an agent that increases PEDF activity.

In one embodiment, the agent comprises an isolated peptide. In one embodiment, the agent comprises full-length PEDF. In one embodiment, the isolated peptide comprises a PEDF-derived peptide. In one embodiment, the PEDF-derived peptide comprises an amino acid sequenced selected from SEQ ID NOs: 1-5.

In one embodiment, the agent comprises an isolated nucleic acid. In one embodiment, the isolated nucleic acid encodes full-length PEDF. In one embodiment, the isolated nucleic acid encodes a PEDF-derived peptide. In one embodiment, the PEDF-derived peptide comprises an amino acid sequenced selected from SEQ ID NOs: 1-5.

In one embodiment, the condition is selected from the group consisting of osteogenesis imperfecta, osteoporosis, osteoarthritis, bone fracture, and cancer of the bone.

The present invention provides a method of treating or preventing a condition associated with reduced bone mass in a subject in need thereof, the method comprising the steps of differentiating a stem cell into the osteoblast lineage by culturing the stem cell in the presence of a composition comprising an agent that increases PEDF activity, thereby producing a population of osteoblasts; and transplanting the population of osteoblasts to the subject.

In one embodiment, the condition is selected from the group consisting of osteogenesis imperfecta, osteoporosis, osteoarthritis, bone fracture, and cancer of the bone.

In one embodiment, the agent comprises an isolated peptide. In one embodiment, the agent comprises full-length PEDF. In one embodiment, the isolated peptide comprises a PEDF-derived peptide. In one embodiment, the PEDF-derived peptide comprises an amino acid sequenced selected from SEQ ID NOs: 1-5.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A through FIG. 1E, depicts the results of example experiments demonstrating that PEDF suppresses adipogenesis. FIG. 1A: MSCs derived from SVCs from the subcutaneous fat pads of WT and PEDF KO mice undergo adipogenesis by day 8, as demonstrated by Oil Red O staining. FIG. 1B: MSCs from WT mice were treated with vehicle or PEDF (500 ng/ml/d) and assessed for adipocyte differentiation, represented by Oil Red O staining, on day 8. FIG. 1C: Treatment with PEDF starting on day 1 of differentiation significantly suppressed multiple proadipogenic transcription factors and adipocyte-specific markers. FIG. 1D: Proadipogenic transcription factor PPARg and its cofactor, PGC1a, were significantly higher in PEDF KO compared with WT MSCs at baseline. PEDF inhibited PPARg and PGC1a expression in WT and KO SVCs when PEDF was initiated on day 3 of differentiation. FIG. 1E: PEDF inhibits adipogenesis of hMSCs. PEDF was started on day 0 of differentiation, and cells were differentiated in adipogenic medium for 10 days. Ad, adipocyte differentiation medium; vehicle, PBS.

FIG. 2A and FIG. 2B, depicts the results of example experiments demonstrating that PEDF expression is markedly suppressed during adipogenesis. FIG. 2A: PEDF expression from FACS-sorted adipocyte precursors and mature adipocytes derived from subcutaneous fat. FIG. 2B: Analysis of unbiased microarray analyses of SVCs undergoing adipogenesis was interrogated for PEDF expression. PEDF expression was reduced by 90% after SVC conversion to mature adipocytes.

FIG. 3A through FIG. 3C, depicts the results of example experiments demonstrating that PEDF enhances osteoblast mineralization and differentiation. FIG. 3A: PEDF KO SVCs were placed in osteoblast differentiation medium for 21 days and stained with Alizarin Red (top panels). KO SVCs were treated with vehicle or PEDF (500 ng/ml/d) starting on day 2 of osteoblast differentiation, and gene expression evaluated on day 21. Differences in Runx2 or collagen 1a1 expression were not seen with PEDF, while PEDF significantly suppressed TGF-β and PPARγ expression. FIG. 3B: hMSCs demonstrate increased alkaline phosphatase staining with PEDF. FIG. 3C: Osteoblast progenitors from WT and PEDF KO mice display increased alkaline phosphatase staining in response to PEDF. Os, osteoblast differentiation medium.

FIG. 4A through FIG. 4D, depicts the results of example experiments demonstrating that PEDF activates Wnt signaling in hMSCs. FIG. 4A: hMSCs were treated with Wnt3a (50 ng/ml) and PEDF (500 ng/ml) and immunoblotted for phosphorylated LRP6. FIG. 4B: hMSCs were treated with IWP-2 (2 µM) for 24 and 48 hours and then challenged with PEDF (500 ng/ml in basal medium). Blots are representative of n=4 experiments/condition. Vehicle was PBS for Wnt3a and PEDF experiments; DMSO for IWP-2 experiments. FIG. 4C: Committed preadipocytes, 3T3-L1 cells, transfected with vector and shRNA targeting LRP6 were assessed for knockdown of LRP6. FIG. 4D: Adding PEDF significantly suppressed PPARγ in vector-transfected cells, while LRP6 knockdown resulted in increased PPARγ expression.

FIG. 5A through FIG. 5E, depicts the results of example experiments demonstrating that PEDF deletion is associated with increased total body adiposity and reduced bone mineral content in mice. FIG. 5A: Body weight and percentage of total body fat by MR spectroscopy of 12-wk-old WT and PEDF KO mice. FIG. 5B: Representative images of WT and PEDF KO subcutaneous (top left panel) and epididymal (bottom left panel) fat pads, and corresponding quantification of subcutaneous white adipose tissue (SWAT), epididymal white adipose tissue (EWAT), and retroperitoneal white adipose tissue (RWAT) under normal feeding and 1 week of a high-fat diet (right panels). FIG. 5C: MicroCT-obtained images of trabecular, dorsal, and lateral surface bone morphology of distal femurs: left panels, cross-section; left center panels, dorsal frontal view; right center panels, left lateral surface; right panels, cut left lateral view. FIG. 5D: Quantification of trabecular bone volume (BV), total volume (TV), and BV/TV, demonstrating diminished trabecular volumes in PEDF KO bones. FIG. 5E: Low-power (4×) and high-power (10×) images of Goldner's stained tibiae and femurs from WT and PEDF KO mice. Decreased epiphyseal and chondro-osseous mineral content in 14-d-old KO compared with WT mice (arrows). Older (26-d-old) mice demonstrate hypomineralization in the epiphysis (short arrows) and chondro-osseous junction (longer arrows) with a diminished proliferative (P) zone; n=6-9 mice for adipose tissue determination and n=3-4 mice for bone imaging.

FIG. 6, comprising FIG. 6A is an illustration demonstrating that PEDF directs MSC fate toward osteoblasts and away from adipocytes in early MSCs. This occurs through its action as a Wnt-β-catenin agonist that suppresses PPARγ. FIG. 6B is an illustration demonstrating that PEDF has biphasic effects on MSC to osteoblast differentiation. In early MSCs, PEDF serves as a redundant Wnt agonist. In the terminal phases of osteoblast differentiation, PEDF antagonizes Wnt3a mediated effects to induce terminal osteoblast differentiation. Wnt3a ligand directs mesenchymal stem cells (MSC) to the osteoblast lineage but unopposed Wnt3a impedes terminal osteoblast differentiation and normal mineralization. PEDF allows for osteoblast precursors to differentiate into mature osteoblasts through Wnt blockade.

FIG. 14A through FIG. 14D, depicts the results of example experiments demonstrating that PEDF peptides added in the final phase (last 8 of 21 days) stimulates mineralization of human MSCs (hMSCs). FIG. 14A: Temporal quantitation of endogenously secreted PEDF from hMSCs over 21 days in osteogenic media. FIG. 14B: Alizarin red staining of 21-day-old hMSC cultures with continuous Wnt3a (50 ng/ml) exposure versus controls demonstrates that continuous and unopposed Wnt3a leads to diminished mineralization. FIG. 14C: Alizarin red staining of 21-day-old hMSC cultures with continuous Wnt3a 50 ng/ml alone or in combination with 100 nM PEDF 34-mer (SEQ ID NO: 1), or mutated K→A peptide (SEQ ID NO: 4). For "late" groups, PEDF 34-mer was added only during the last 8 days of the differentiation protocol. FIG. 14D: Quantitation of Alizarin red staining in FIG. 14C demonstrates gain of function properties with K→A mutated PEDF 34-mer over the native PEDF and that addition of this mutated peptide in the last eight days of differentiation provides osteoblast mineralization comparable to the full-length protein added for 21 days. n=3-4 wells/group. *=$p<0.05$, **=$p<0.01$ by Student's t-test compared to Wnt3a group. One way ANOVA p=0.0022.

DETAILED DESCRIPTION

Figure 1:
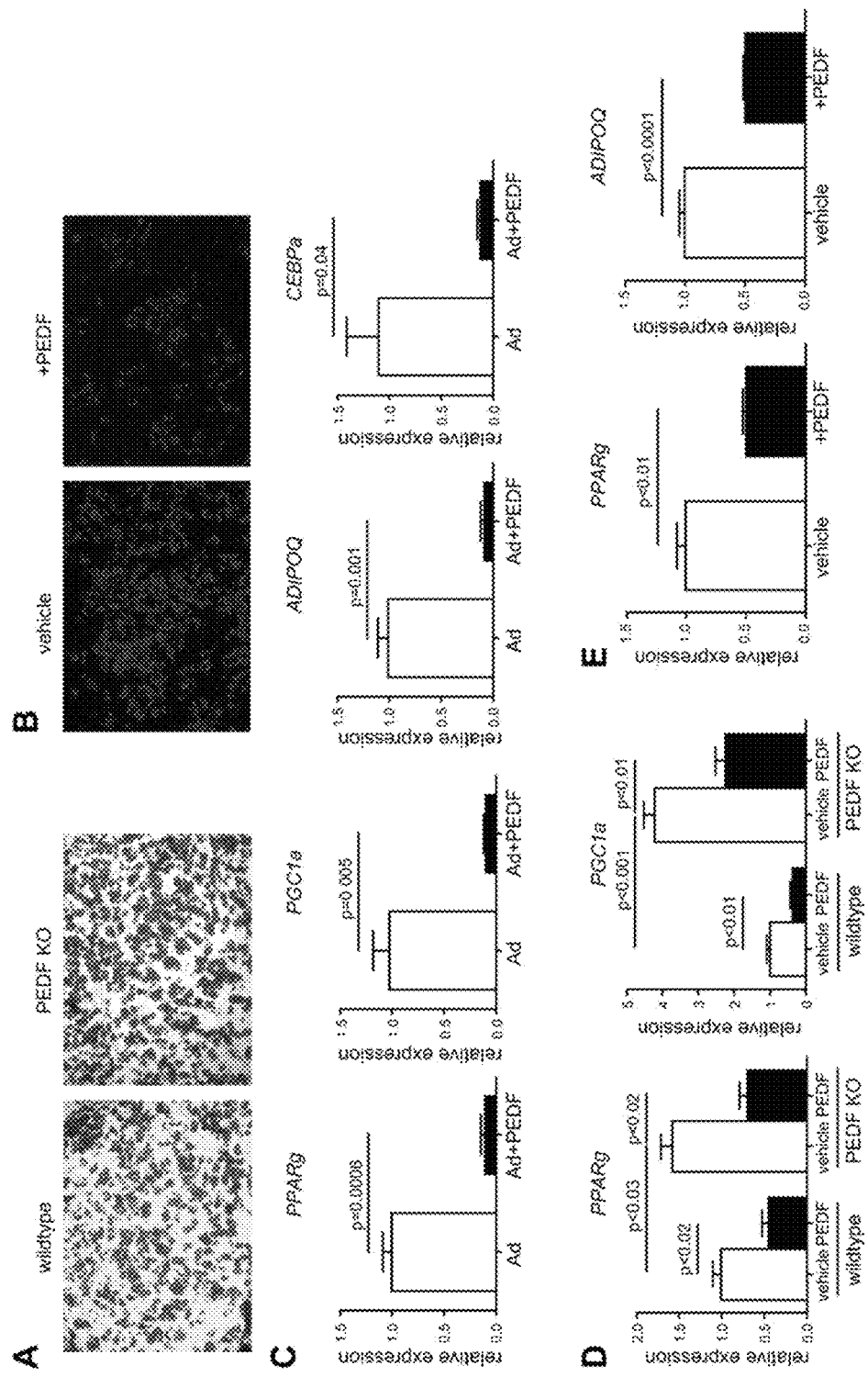
FIG. 1, comprising

In one aspect, the present invention provides compositions for differentiating a stem cell into an osteoblast progenitor cell or osteoblast. In certain embodiments, the composition of the invention may be used for promoting bone formation and increasing bone mass. In one embodiment, the composition comprises an agent, for example, an isolated nucleic acid, isolated peptide, small molecule, peptidomimetic, or the like, which increases PEDF expression, PEDF activity, or both. In one embodiment, the composition comprises full-length PEDF. In one embodiment, the composition comprises recombinant PEDF. In one embodiment, the composition comprises a PEDF fragment or a PEDF-derived peptide.

In certain embodiments, the present invention provides methods for differentiating a stem cell into an osteoblast progenitor cell or osteoblast. For example, in certain embodiments, the method comprises contacting a stem cell with a composition comprising an agent that increases PEDF expression, PEDF activity, or both.

In certain embodiments, the present invention provides methods for increasing bone mass in a subject in need thereof. For example, in certain embodiments, the invention provides treating a subject having, or at risk for developing, a condition associated with reduced bone mass or reduced bone formation. Exemplary conditions, include, but are not limited to osteogenesis imperfecta, osteoporosis, osteoarthritis, bone fracture, and cancer of the bone. In one embodiment, the condition is osteogenesis imperfecta Type VI. In one embodiment, the method comprises contacting the subject with a composition comprising an agent that increases PEDF expression, PEDF activity, or both.

In one embodiment, the method comprises contacting a cell with the composition ex vivo to promote the differentiation of the cell into the osteoblast lineage. In one embodiment, the method comprises transplanting one or more differentiated cells, or progeny thereof, to a treatment site in need of increased bone mass in the subject.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of stem cells in a substantially undifferentiated state can be employed.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "differentiated cell" is meant any primary cell that is not, in its native form, pluripotent as that term is defined herein. Stated another way, the term "differentiated cell" refers to a cell of a more specialized cell type derived from a cell of a less specialized cell type (e.g., a stem cell such as an induced pluripotent stem cell) in a cellular differentiation process.

"Differentiation medium" is used herein to refer to a cell growth medium comprising an additive or a lack of an additive such that a stem cell or other such progenitor cell, that is not fully differentiated, develops into a cell with some or all of the characteristics of a differentiated cell when incubated in the medium.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235, 970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCRTM, and the like, and by synthetic means.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

As used herein, the phrase "stem cells" refers both to the earliest renewable cell population responsible for generating cell mass in a tissue or body and the very early progenitor cells, which are somewhat more differentiated, yet are not committed and can readily revert to become a part of the earliest renewable cell population.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based in part on the discovery that PEDF, PEDF peptide fragments, and PEDF-derived peptides induce mesenchymal stem cell (MSC) differentiation to the osteoblast lineage.

In one embodiment, the invention provides compositions for producing an osteoblast progenitor cell or osteoblast, where the composition comprises an agent which increases PEDF expression, PEDF activity, or both. In one embodiment, the composition comprises PEDF. In one embodiment, the composition comprises an isolated nucleic acid encoding PEDF. In certain embodiments, the composition comprises a PEDF-derived peptide. In one embodiment, the composition comprises an isolated nucleic acid encoding a PEDF-derived peptide. For example, the present invention is based in part upon the identification of the region within PEDF which mediates MSC differentiation into the osteoblast lineage. It is demonstrated herein that PEDF fragments and PEDF-derived peptides thereof mimic PEDF mediated MSC differentiation into the osteoblast lineage. In certain embodiments, the PEDF-derived peptide comprises an amino acid sequence selected from DPFFKVPVNK-LAAAVSNFGYDLYRVRSSTSPTTN (SEQ ID NO: 1), DPFFKVPVNKIAAAVSNFGYDLYRVRSSTSPTTN (SEQ ID NO: 2), DPFFKVPVNKEAAAVSNFGYD-LYRVRSSTSPTTN (SEQ ID NO: 3) DPFFKVPVNAL-AAAVSNFGYDLYRVRSSTSPTTN (SEQ ID NO: 4), OR DPFFKVPVNAIKAAVSNFGYDLYRVRSSTSPTTNAIK (SEQ ID NO: 5).

In one embodiment, the invention provides a method for producing an osteoblast progenitor cell or osteoblast. For example, in one embodiment, the method comprises differentiating a stem cell into the osteoblast lineage by culturing the stem cell in the presence of a composition which increases PEDF expression, PEDF activity, or both.

In one embodiment, the invention provides a method for increasing bone mass in a subject in need thereof. In one embodiment, the method comprises administering to the subject a composition which increases PEDF expression, PEDF activity, or both. For example, it is demonstrated herein that PEDF administration increases bone mass in vivo.

In certain embodiments, the method comprises transplanting one or more differentiated osteoblasts or osteoblast progenitor cells, or progeny thereof, to a treatment site of the subject. For example, in one aspect, the method comprises obtaining a stem cell from the subject, and culturing the stem cell in the presence of a composition which increases PEDF expression, PEDF activity, or both, thereby producing one or more differentiated osteoblasts or osteoblast progenitor cells. In certain embodiments, the method comprises administering the composition only during final stages of stem cell differentiation.

In one embodiment, the invention provides a method for treating a disease or condition associated with increased fat, including, but not limited to diabetes, obesity, metabolic syndrome, and the like. For example, it is demonstrated herein that PEDF, PEDF fragments, and PEDF-derived peptides promote MSC differentiation into osteoblasts and inhibit MSC differentiation into adipocytes. Thus, in certain aspects, the compositions and methods of the present invention can reduce adipocyte and fat production, thereby treating a disease or condition associated with increased fat.

Compositions

In one aspect, the present invention provides compositions for differentiating a stem cell into the osteoblast lineage. For example, in certain instances the compositions promote the differentiation of a mesenchymal stem cell (MSC) into the osteoblast linage. The compositions, may be used, for example, to promote bone repair, promote bone formation, and increase bone mass. In certain embodiments, the composition comprises an agent that increases PEDF expression, PEDF activity, or both. Exemplary agents, include, but are not limited to, isolated nucleic acids, vectors, isolated peptides, peptide mimetics, small molecules, and the like.

An agent that increases PEDF activity is any agent that increases the normal endogenous activity associated with PEDF protein. In certain embodiments, the agent modulates the level or activity of a PEDF-encoding nucleic acid molecule or PEDF by modulating the transcription, translation, splicing, degradation, enzymatic activity, binding activity, or combinations thereof, of PEDF-encoding nucleic acid molecule or PEDF. In certain embodiments, the agent increases the expression of PEDF, thereby increasing PEDF activity. In certain embodiments, the agent increases the activity of endogenous PEDF protein. In certain embodiments, the agent has activity that mimics the normal endogenous activity associated with PEDF protein. For example, in certain embodiments, the composition of the present invention comprises isolated peptide fragments and PEDF-derived peptides that mimic endogenous PEDF activity.

In one embodiment, the composition of the present invention comprises an isolated peptide comprising PEDF, or biologically functional fragment thereof. The composition may comprise, for example, any isoform of PEDF, including PEDF from any organism. In one embodiment, the composition comprises full-length PEDF. In one embodiment, the composition comprises recombinant PEDF.

In one embodiment, the isolated peptide comprises human PEDF, or biologically functional fragment thereof. Exemplary human PEDF amino acid sequences include, but are not limited to, amino acid sequences of GenBank Accession No. NP_002606.3, GenBank Accession No. AAA60058.1, GenBank Accession No. EAW90577.1, GenBank Accession No. AAK9249.1, GenBank Accession No. AAH13984.1, GenBank Accession No. AAH00522.1, GenBank Accession No. BAJ83968.1, GenBank Accession No. BAJ83967.1, GenBank Accession No. BAJ83966.1, GenBank Accession No. AAT08033.1 GenBank Accession No. AAP35886.1, and GenBank Accession No. CAJ34133.1. However, the present invention is not limited to these particular sequences. Rather the present invention encompasses any PEDF isoform from any source.

In one embodiment, composition comprises an isolated PEDF-derived peptide. In one embodiment, the PEDF-derived peptide comprises a fragment of PEDF that mimics the ability of PEDF to stimulate the differentiation of a stem cell into the osteoblast lineage. In one embodiment, the PEDF-derived peptide comprises a derivative of the PEDF fragment. In certain embodiments, the isolated peptide of the composition comprises an amino acid sequence selected from DPFFKVPVNKLAAAVSNFGYDLYRVRSSTSPTTN (SEQ ID NO: 1), DPFFKVPVNKIAAAVSNFGYDLYRVRSSTSPTTN (SEQ ID NO: 2), DPFFKVPVNKEAAAVSNFGYDLYRVRSSTSPTTN (SEQ ID NO: 3) DPFFKVPVNALAAAVSNFGYDLYRVRSSTSPTTN (SEQ ID NO: 4), OR DPFFKVPVNAIKAAVSNFGYDLYRVRSSTSPTTNAIK (SEQ ID NO: 5).

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The invention should also be construed to include any form of a peptide having substantial homology to PEDF or a PEDF-derived peptide disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of PEDF or a PEDF-derived peptide disclosed herein.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to stimulate the differentiation of a stem cell into the osteoblast lineage. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of PEDF or a PEDF-derived peptide.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides comprising PEDF or a PEDF-derived peptide fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue (e.g., bone, regenerating bone, degenerating bone, cartilage). A targeting domain may target the peptide of the invention to a cellular component.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the PEDF peptide or PEDF-derived peptide fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

In one embodiment, the present invention provides a composition comprising an isolated nucleic acid encoding PEDF, a PEDF-derived peptide, or a biologically functional fragment thereof.

In certain embodiments, the composition increases the expression of a biologically functional fragment of PEDF. For example, in one embodiment, the composition comprises an isolated nucleic acid sequence encoding a biologically functional fragment of PEDF. As would be understood in the art, a biologically functional fragment is a portion or portions of a full length sequence that retain the biological function of the full length sequence. Thus, a biologically functional fragment of PEDF comprises a peptide that retains the function of full length PEDF.

In one embodiment, the isolated nucleic acid sequence encodes PEDF. In various embodiments, the isolated nucleic acid sequence encodes a PEDF-derived peptide comprising an amino acid sequence selected from SEQ ID NOs:

```
                                          (SEQ ID NO: 1)
DPFFKVPVNKLAAAVSNFGYDLYRVRSSTSPTTN, (SEQ ID NO: 2)
DPFFKVPVNKIAAAVSNFGYDLYRVRSSTSPTTN, (SEQ ID NO: 3)
DPFFKVPVNKEAAAVSNFGYDLYRVRSSTSPTTN (SEQ ID NO: 4)
DPFFKVPVNALAAAVSNFGYDLYRVRSSTSPTTN,
OR (SEQ ID NO: 5)
DPFFKVPVNAIKAAAVSNFGYDLYRVRSSTSPTTNAIK.
```

Further, the invention encompasses an isolated nucleic acid encoding a peptide having substantial homology to PEDF or a PEDF-derived peptide disclosed herein. In certain embodiments, the isolated nucleic acid sequence encodes PEDF or a PEDF peptide mimetic having at least 75%, 80%, 85%, 90%, 95%, 96%, 97%, 98%, or 99% sequence homology with an amino acid sequence selected from SEQ NOs: 1-5.

The isolated nucleic acid sequence encoding PEDF or a PEDF-derived peptide can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding PEDF or a PEDF-derived peptide, or functional fragment thereof. In one embodiment, the composition comprises an isolated RNA molecule encoding PEDF or a PEDF-derived peptide, or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O— and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O- dimethylaminoethyloxyethyl (2'-O-DMAEOE), or 2'-O-N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

In certain embodiments, the nucleic acid molecule of the invention preferably has one or more of the following properties:

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding PEDF or a PEDF-derived peptide is typically achieved by operably linking a nucleic acid encoding the PEDF or a PEDF-derived peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of PEDF or a PEDF-derived peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the present invention provides a delivery vehicle comprising PEDF, a PEDF-derived peptide, or a nucleic acid molecule encoding PEDF or a PEDF-derived peptide. Exemplary delivery vehicles include, but are not limited to, microspheres, microparticles, nanoparticles, polymerosomes, liposomes, and micelles. For example, in certain embodiments, the delivery vehicle is loaded with PEDF, a PEDF-derived peptide, or a nucleic acid molecule encoding PEDF or a PEDF-derived peptide. In certain embodiments, the delivery vehicle provides for controlled release, delayed release, or continual release of its loaded cargo. In certain embodiments, the delivery vehicle comprises a targeting moiety that targets the delivery vehicle to a treatment site.

In one embodiment, the present invention provides a cell or population of cells derived from the differentiation of a stem cell. In one embodiment, the cell is an osteoblast or osteoblast progenitor cell, derived from a stem cell. For example, it is described herein that PEDF and PEDF-derived peptides described herein stimulate the differentiation of a stem cell into the osteoblast lineage. The stem cell from which the cell or cell population of the invention is derived, may be any type of stem cell, including, but not limited to, embryonic stem cell, adult stem cell, cord blood stem cell, cord tissue derived stem cell, induced pluripotent stem cell, and the like. In one embodiment, the stem cell is a mesenchymal stem cell (MSC). In one embodiment, the stem cell is a human mesenchymal stem cell.

In one embodiment, the osteoblast or osteoblast progenitor cell of the invention is derived by contacting a stem cell with an agent that stimulates PEDF expression, PEDF activity or both. In certain embodiments, the stem cell is a mesenchymal stem cell (MSC). For example, in one embodiment, the osteoblast or osteoblast progenitor cell is derived by culturing a stem cell in the presence of PEDF or PEDF-derived peptide. In one embodiment, the stem cell is cultured in a differentiation medium comprising PEDF or PEDF peptide mimetic. In one embodiment, the stem cell is cultured in the presence of a cell expressing and secreting PEDF or PEDF-derived peptide. For example, the stem cell may be cultured in the presence of a genetically modified cell, modified with an isolated nucleic acid to express and secrete PEDF or PEDF-derived peptide.

In certain aspects, the differentiated osteoblast or osteoblast progenitor cells may be used in the treatment of a condition associated with reduced bone mass or reduced bone formation. In one embodiment, the differentiated osteoblast or osteoblast progenitor cells may be used as research tools, used for example in drug discovery toxicity testing, disease pathology, and the like.

In one embodiment, the present invention provides a differentiation medium comprising an agent that increases PEDF expression, PEDF activity, or both. For example, in one embodiment, the differentiation medium comprises PEDF or a PEDF-derived peptide. The differentiation medium may comprise additional differentiation agents, including but not limited to $Ca^{2+}$, an epidermal growth factor (EGF), a platelet derived growth factor (PDGF), a keratinocyte growth factor (KGF), a transforming growth factor (TGF), cytokines such as an interleukin, an interferon, or tumor necrosis factor, retinoic acid, transferrin, hormones (e.g., androgen, estrogen, insulin, prolactin, triiodothyronine, hydrocortisone, or dexamethasone), sodium butyrate, TPA, DMSO, NMF (N-methyl formamide), DMF (dimethylformamide), or matrix elements such as collagen, laminin, heparan sulfate). The differentiation medium may also comprise one or more of pituitary extract (e.g. a bovine pituitary extract), steroid hormones (e.g. hydrocortisone, or a salt thereof such as the acetate), growth factors (e.g., epidermal growth factor, preferably human epidermal growth factor), catecholamines (e.g., epinephrine, either in racemic or enantiomeric form), iron-binding proteins (e.g., a transferrin), insulin, vitamins (e.g., retinoic acid), thyroid hormones (e.g., triiodothyronine), serum albumins (e.g., bovine or human serum albumin, including recombinant preparations), antibiotics (e.g., aminoglycoside antibiotics, such as gentamicin), and/or antifungals (e.g., amphotericin-B). In certain embodiments, the differentiation medium comprises one or more agents typically found in osteogenic differentiation medium, including but not limited to dexamethasone, ascorbic acid, and β-glycerophosphate The present invention provides a scaffold or substrate composition comprising PEDF, a PEDF-derived peptide, a nucleic acid molecule encoding PEDF or a PEDF-derived peptide, a cell producing PEDF or PEDF-derived peptide, an osteoblast or osteoblast progenitor cell, or a combination thereof. For example, in one embodiment, PEDF, a PEDF-derived peptide, a nucleic acid molecule encoding PEDF or a PEDF-derived peptide, a cell producing PEDF or PEDF-derived peptide, an osteoblast or osteoblast progenitor cell, or a combination thereof within a scaffold. In another embodiment, PEDF, a PEDF-derived peptide, a cell producing PEDF or PEDF-derived peptide, a nucleic acid molecule encoding PEDF or a PEDF-derived peptide, an osteoblast or osteoblast progenitor cell, or a combination thereof is applied to the surface of a scaffold. The scaffold of the invention may be of any type known in the art. Non-limiting examples of such a scaffold includes a, hydrogel, electrospun scaffold, foam, mesh, sheet, patch, and sponge.

The present invention also provides pharmaceutical compositions comprising one or more of the compositions described herein. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, intratumoral, subcutaneous, intramuscular, or intraperitoneal injection, or by infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the HMW-HA or other composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Methods of Producing an Osteoblast

In one aspect, the present invention provides a method of generating an osteoblast or osteoblast progenitor cell. For example, it is demonstrated herein that PEDF and PEDF-derived peptides induce the differentiation of a stem cell (e.g., a MSC) to differentiate into the osteoblast lineage.

The production of a population of in vitro cultured cells of osteoblast lineage derived from at least one stem cell includes culturing at least stem cell in vitro according to the method of the invention in order to produce differentiated cells. In one embodiment, the method of production further includes identifying the differentiated cells of osteoblast phenotype by detecting expression of at least one biomarker of osteoblasts or osteoblast progenitor cells, and isolating the differentiated cells having osteoblast phenotype. In some cases, this may include selecting a purified population of differentiated cells wherein at least 95%, preferably at least 96%, preferably at least 97%, more preferably at least 98%, more preferably at least 99% of the cells have osteoblast or osteoblast progenitor phenotype.

The cells of the invention and cells derived therefrom can be derived from, inter alia, humans, primates, rodents and birds. Preferably, the cells of the invention are derived from mammals, especially mice, rats and humans. Stem cells from which the osteoblasts or osteoblast progenitor cells are derived may be either wild-type or genetically modified stem cells.

The cells of the present invention, whether grown in suspension or as adherent cell cultures, are grown in contact with culture media.

Culture media used in the present invention preferably comprise a basal medium, optionally supplemented with additional components.

Basal medium is a medium that supplies essential sources of carbon and/or vitamins and/or minerals for the cells. The basal medium is generally free of protein and incapable on its own of supporting self-renewal/symmetrical division of the cells.

Preferably, the suitable cell is isolated from a mammal, more preferably a primate and more preferably still, a human. The cells useful in the methods of the present invention are isolated using methods known in the art. Following isolation, the suitable cells are cultured in a culture medium. Media formulations that support the growth of cells include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E-with Earle's salt base), Medium M199 (M199H-with Hank's salt base), Minimum Essential Medium Eagle (MEM-E-with Earle's salt base), Minimum Essential Medium Eagle (MEM-H-with Hank's salt base) and Minimum Essential Medium Eagle (MEM-NAA with nonessential amino acids), and the like.

In certain embodiments, the cells are cultured in a differentiation medium, which include one or more agents that aid in the differentiation of a cell. For example, in one embodiment, the cells are cultured in an osteogenic differentiation medium, which comprises one or more agents that aid in the differentiation of the cell into the osteoblast lineage. An exemplary osteogenic differentiation medium is the Osteocyte Differentiation Tool (ATCC° PCS-500-052™)

It is further recognized that additional components may be added to the culture medium. Such components include, but are not limited to, antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 μg/ml. However, the invention should in no way be construed to be limited to any one medium for culturing the cells of the invention. Rather, any media capable of supporting the cells of the invention in tissue culture may be used.

In certain embodiments, the culture media comprises an agent that increases PEDF expression, PEDF activity, or both. For example, the media may comprise an isolated PEDF peptide, a PEDF-derived peptide, or derivatives and fragments thereof. In certain embodiments, the method comprises culturing the stem cells in the presence of an agent that increases PEDF expression, PEDF activity, or both only during final stages of stem cell differentiation. For example, in certain embodiments, differentiation of the stem cell occurs over about 15-25 days in culture. In one embodiment, differentiation of the stem cell occurs over about 18-22 days in culture. differentiation of the stem cell occurs over about 21 days in culture. For example, in certain embodiments, the agent that increases PEDF expression, PEDF activity, or both is administered only during the last 1-12 days of culture. In one embodiment, the agent that increases PEDF expression, PEDF activity, or both is administered only during the last 5-10 days of culture. In one embodiment, the agent that increases PEDF expression, PEDF activity, or both is administered only during the last 8 days of culture.

In certain embodiments, culture media used in the invention do not contain any components which are undefined (e.g., serum and/or feeder cells), that is to say components whose content is unknown or which may contain undefined or varying factors that are unspecified. An advantage of using fully defined media, free of serum and free of serum extracts, is that efficient and consistent protocols for culture and subsequent manipulation of the cells of the invention and cells derived therefrom can be obtained.

Typical substrates for culture of the cells in all aspects of the invention are culture surfaces recognized in this field as useful for cell culture, and these include surfaces of plastics, metal, composites, though commonly a surface such as a plastic tissue culture plate, widely commercially available, is used. Such plates are often a few centimeters in diameter. For scale up, this type of plate can be used at much larger diameters and many repeat plate units used.

The culture surface may further comprise a cell adhesion protein, usually coated onto the surface. Receptors or other molecules present on the cells bind to the protein or other cell culture substrate and this promotes adhesion to the surface and promotes growth. In certain embodiments, the cultures of the invention are preferably adherent cultures, i.e. the cells are attached to a substrate.

In certain aspects the cells from which the osteoblasts or osteoblast progenitor cells are derived, are cultured in the presence of one or more additional cells that support the growth or differentiation of the cells. For example, the cells from which the osteoblasts or osteoblast progenitor cells are derived may be co-cultured with one or more cells genetically modified to express a PEDF peptide or PEDF-derived peptide.

Treatment Methods

The present invention provides a method for the treatment or prevention of a condition associated with reduced bone formation or reduced bone mass in a subject in need thereof. Exemplary conditions treated or prevented by way of the present invention includes, but is not limited to osteogenesis imperfecta, osteoporosis, osteoarthritis, bone fracture, and cancer of the bone. In one embodiment, the condition is osteogenesis imperfecta Type VI.

In certain embodiments, the method comprises administering an effective amount of a composition described herein to a subject diagnosed with, suspected of having, or at risk for developing a condition associated with reduced bone formation or reduced bone mass. In certain aspects, the composition is contacted to a cell or tissue where diseased bone is present or at risk for developing. In one embodiment, the composition is administered systemically to the subject.

The composition of the invention may be administered to a patient or subject in need in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

In certain embodiments, the composition of the invention is administered during surgical resection or debulking of a tumor or diseased tissue. For example, in subjects undergoing surgical treatment of diseased tissue or tumor, the composition may be administered to the site in order to further treat the tumor or promote bone growth.

In one embodiment, the method comprises administering to the subject a scaffold comprising PEDF, a PEDF-derived peptide, a cell modified to express PEDF or a PEDF-derived peptide, or a differentiated osteoblast.

Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "therapeutic amount" is indicated, the precise amount of the compositions of the present invention to be administered can be determined by a physician with consideration of individual differences in age, weight, disease type, extent of disease, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are preferably administered by i.v. injection.

In one embodiment, the invention provides a method of treating a condition associated with reduced bone formation or reduced bone mass in a subject comprising transplanting a population of differentiated stem cells, or progeny thereof of the invention into the mammal. In certain aspects, the method comprises transplanting to a treatment site that contains injured or diseased bone, a population of differentiated stem cells, or progeny thereof, at least 95% of which have osteoblast or osteoblast progenitor cell phenotype. The population of cells is prepared in accordance with a method described herein, and is effective to repair at least a portion of the injured or diseased bone.

In some embodiments, at least one differentiated stem cell, or progeny thereof, comprises a therapeutic transgene operably linked to a cell-specific promoter, wherein the transgene encodes a therapeutic gene product.

In some embodiments, an above-described population of cells is transplanted directly to injured or diseased bone. In some embodiments, transplanting the population of cells comprises administering a substrate or scaffold comprising the cells onto or into the bone. In one embodiment, the population of differentiated stem cells, or progeny thereof of the invention is at least 95%, preferably at least 96%, preferably at least 97%, more preferably at least 98%, more preferably at least 99% of which exhibit osteoblast or osteoblast progenitor phenotype, wherein the population of cells is prepared in accordance with the methods of the invention, and is effective to promote bone formation, promote bone repair, or increase bone mass at the treatment site.

Methods of treatment of the diseases encompassed by the invention can comprise the transplantation of single cells, cell lines, compositions, or cell populations of the invention into a subject in need thereof In certain embodiments, the subject is a human.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

PEDF Modulates MSC Differentiation

Pigment epithelium-derived factor (PEDF), the protein product of the SERPINF lgene, has been linked to distinct diseases involving adipose or bone tissue, the metabolic syndrome, and osteogenesis imperfecta (OI) type VI. Since mesenchymal stem cell (MSC) differentiation into adipocytes versus osteoblasts can be regulated by specific factors, PEDF-directed dependency of murine and human MSCs was assessed. PEDF inhibited adipogenesis and promoted osteoblast differentiation of murine MSCs, osteoblast precursors, and human MSCs. Blockade of adipogenesis by PEDF suppressed peroxisome proliferator-activated receptor-γ (PPARγ), adiponectin, and other adipocyte markers by nearly 90% compared with control-treated cells (P<0.001). Differentiation to osteoblasts by PEDF resulted in a common pathway that involved PPARγ suppression (P<0.01). Canonical Wnt-β-catenin signaling results in a MSC differentiation pattern analogous to that seen with PEDF. Thus, adding PEDF enhanced Wnt-β-catenin signal transduction in human MSCs, demonstrating a novel Wnt agonist function. In PEDF knockout (KO) mice, total body adiposity was increased by >50% compared with controls, illustrating its systemic role as a negative regulator of adipogenesis. Bones from KO mice demonstrated a reduction in mineral content recapitulating the OI type VI phenotype. These results demonstrate that the human diseases associated with PEDF reflect its ability to modulate MSC differentiation.

The materials and methods employed in these experiments are now described.

Chemicals

The inhibitor of Wnt production (IWP-2; Tocris Bioscience, Minneapolis, Minn., USA; 2 μM×24-48 h) was used to block production of endogenous Wnt proteins (Chen et al., 2009, Nat Chem Biol, 5: 100-107; Clevers et al., 2012, Cell, 149: 1192-1205). All other chemicals, unless indicated, were purchased from Sigma (St. Louis, Mo., USA).

Animals

PEDF KO mice have been described previously (Doll et al., 2003, Nat Med, 9: 774-780). PEDF KO mice were bred with wild-type (WT) mice to generate heterozygous breeding pairs. Mice were backcrossed for >10 generations to generate KO and WT breeding pairs. Mice were maintained in normal specific pathogen-free conditions on a 12/12-h light-dark cycle and fed with a standard mouse chow diet ad libitum. Tibiae and femurs from 14- and 26-d-old mice were processed. A high-fat diet (45% calories from fat; Research Diets, New Brunswick, N.J., USA) was given for 1 week where indicated.

Primary Cells

Subcutaneous fat pads were dissected from WT and PEDF-KO mice and digested in HBSS medium containing 3% BSA (American Bioanalytical, Natick, Mass., USA), 0.8 mg/ml of type 2 collagenase (Worthington Biochemical Corp., Lakewood, N.J., USA), 1.2 mM $CaCl_2$, and 1.0 mM $MgCl_2$ for 1 h and 15 min in a shaking 37° C. water bath. Stromovascular fractions (SVFs) were obtained after centrifugation at 300 g for 5 min. Cells were initially plated in proliferation medium (DMEM plus 10% FBS and bFGF; 1 ng/ml) until 70-80% confluence. Adipogenic differentiation was initiated with differentiation medium (5 µg/ml insulin, 10 nM dexamethasone, 0.5 mM IBMX, and 1 µM rosiglitazone) and added on d 0 for 72 h. Afterward, cells were maintained in DMEM with 10% FBS and 5 µg/ml insulin for an additional 5 d until full differentiation as confirmed by light microscopy and Oil Red O staining. Osteoblast differentiation cocktail (10 nM dexamethasone, 50 µg/ml ascorbic acid, and 10 mM β-glycerophosphate) was used for 21 d.

Adipose-derived hMSCs [American Type Culture Collection (ATCC), Manasses, Va., USA; PCS-500-011) were propagated in MSC basal medium supplemented with MSC growth kit (ATCC). Cells were CD29, CD44, CD105, and CD166 positive and negative for CD 31, CD34, and CD45. Interrogation of Wnt-β-catenin signaling was done in ATCC MSC basal medium with 2% FBS. PEDF (500 ng/ml) was added for 6 h. Passage 2 and 3 hMSCs were used for Wnt signaling experiments. For adipocyte conversion, cells (5000 cells/$cm^2$) were placed in adipocyte differentiation medium (ATCC; PCS-500-050) for 9-10 d. For osteoblast differentiation, cells (5000 cells/$cm^2$) were differentiated in osteoblast differentiation medium (ATCC; PCS-500-052) for 10-21 d. Alkaline phosphatase kit (Sigma) was used to stain osteoblasts.

Osteoblast progenitor cells were isolated as described previously (Bakker et al., 2012, Methods Mol Biol, 816: 19-29). Briefly, calvaria were dissected from WT and PEDF KO mice with careful removal of all visible connective tissue surrounding the calvaria. After being washed in HBSS, calvaria were digested in collagenase type 1 (1 mg/ml; Worthington Biochemical) in HBSS for 10 min in a shaking water bath at 37° C. The first collection of supernatant was discarded, and calvaria were digested for an additional 20 min with the second and third sets of supernatants collected. Cells were washed twice in 2% FBS. Osteoblast progenitors were differentiated into osteoblasts in osteoblast differentiation medium for 21 d unless specified. In vitro assays assessing adipocyte or osteoblast differentiation were performed ≥3 separate times, with n=3-4 for each separate experiment.

Sorting of Adipose Populations

Excised white subcutaneous adipose tissue was digested in 0.8 mg/ml collagenase type 2 (Worthington Biochemical; LS004174) in HBSS containing 3% BSA, 1.2 mM $CaCl_2$, 1.0 mM $MgCl_2$, and 0.8 mM $ZnCl_2$ for 75 min in a shaking water bath. Floating adipocytes were separated from the SVF via centrifugation at 300 g for 3 min. Isolation of intact adipocytes was verified by staining with plasma membrane (Cell Mass Orange) and nuclear (DAPI) dyes. Purified adipocytes were then placed into TRIzol LS Reagent (Invitrogen, Grand Island, N.Y., USA; 10296028) for RNA isolation. SVF was sequentially filtered through 70- and 40-µm filters before staining with the following antibodies for 20 min: CD45 APC-eFluor 780 at 1:5000 (eBioscience, San Diego, Calif., USA; 47-0451-80), CD31 PE-Cy7 at 1:1200 (eBioscience; 25-0311-82), CD29 Alexa Fluor 700 at 1:400 (BioLegend, San Diego, Calif., USA; 102218), CD34 Alexa Fluor 647 at 1:200 (BioLegend; 119314), Sca-1 Pacific Blue at 1:1000 (BD Biosciences, San Jose, Calif., USA; 560653). Following antibody incubation, samples were washed and centrifuged at 300 g for 3 min.

PEDF Protein and PEDF Restoration

Full-length recombinant human PEDF was generated in HEK cells (Chung et al., 2008, J Hepatol, 48: 471-478). PEDF integrity was confirmed by silver staining (Invitrogen), and then dialyzed in PBS.

RNA Analysis and Quantitative Reverse Transcriptase Polymerase Chain Reaction (qRT-PCR)

RNA was isolated and processed using the RNAEasy mini kit (Qiagen, Valencia, Calif., USA). Primer probe sets were obtained from a commercial source (Applied Biosystems, Foster City, Calif., USA), and qRT-PCR was performed on a TaqMan ABI 7500 system (Applied Biosystems) as described previously (Schmitz et al., 2011, Am J Pathol, 179: 2990-2999). Target gene expression was normalized against 18S ribosomal RNA using the $\Delta\Delta C_t$ method. On sorted adipose populations, qRT-PCR was performed on a Roche Lightcycler 480 (Roche, Basel, Switzerland) using a SYBR FAST qPCR kit (Kapa Biosystems, Woburn, Mass., USA; KK4611), and target gene expression was normalized to TBK1.

List of Primers

Applied Biosystems TaqMan assays Cat #

PGC1a- Mm01208835_m1

PPARg- Mm00440940_m1

ADIPOQ- Mm00456425_m1

CEBPα- Mm00514283_m1

ALP1- Mm00475834_m1

RUNX2- Mm00501584_m1

COL1A1- Mm00801666_g1

TGFB1- Mm01178820_m1

TSP1- Mm00449022_m1

18S- Mm03928990_g1

List of Primers (Primary Adipose Populations)

```
PEDF-
                            (SEQ ID NO: 6)
      AAGTTCTGGGTCACGGTCAG (SEQ ID NO: 7)
      ACGATACGGCTTGGACTCTG

Adipsin-
                            (SEQ ID NO: 8)
      GGGCGTCTATACCCGAGTGT (SEQ ID NO: 9)
      AGCCACGTGTCTCTGGTGTC
```

TBK1-

AGGGCTTTGTGACGGGAACAG (SEQ ID NO: 10)

GGCACCCGGTCAAATGAGA (SEQ ID NO: 11)

Immunoblotting

Immunoblotting was performed as described previously (Schmitz et al., 2011, Am J Pathol, 179: 2990-2999). Proteins were separated by 10% SDS-PAGE on gradient gels (Bio-Rad, Hercules, Calif., USA). Antibodies against non-phosphorylated β-catenin, total β-catenin, phospho-LRP6 (serine 1490), total LRP6 (Cell Signaling Technologies, Danvers, Mass., USA), and alkaline phosphatase (Developmental Studies Hybridoma Bank, University of Iowa, Iowa City, Iowa, USA). To assess signaling through the Wnt coreceptor LRP6, 3T3 adipocyte precursors with vector and LRP6-KO shRNA were used (Liu et al., 2012, J Biol Chem, 287: 7213-7223). On confluence, cells were serum starved for 48 h, and then changed to DMEM with 10% FCS (d 0). PEDF (10 nM) was added on d 0, and cells were harvested after 48 h. Knockdown was confirmed by immunoblotting for total LRP6. β-actin (Sigma) was used as a loading control.

Staining

For Oil Red O staining, cells were washed in PBS and fixed in 10% formalin for 20 min. Cells were then stained with 0.5% Oil Red O for 15 min. For Alizarin Red staining, cells were washed in PBS and fixed in 10% formalin for 20 min. After being washed twice in ddH$_2$O, cells were stained in 2% Alizarin Red S (pH 4.1). Cells were washed ≥3 times in ddH$_2$O, and images were acquired with a Zeiss Axiophot microscope (Carl Zeiss, Oberkochen, Germany). Representative images are shown at ×40 view.

Bone Micro-Computed Tomography (MicroCT) and Histological Analysis

A ScanCo μCT 35 scanner (ScanCo Medical AG, Brüttisellen, Switzerland; Yale Center Core for Musculoskeletal Disorders) was used to assess the distal femur for trabecular and cortical bone morphology from 21-d-old WT and PEDF-KO mice in a blinded manner. Axial, sagittal, and coronal images were obtained at standardized sites, and measures of trabecular and total bone volumes and other parameters of bone density were obtained (Bouxsein et al., 2010, J Bone Miner Res, 25: 1468-1486). For histology, femurs and tibiae of 14- and 26-d-old mice were dissected, cleaned, and fixed in 70% ethanol, then further dehydrated through graded ethanols, cleared in toluene, and embedded in methyl methacrylate (MMA). After polymerization, MMA blocks were removed from the mold, cut to size, sanded, and polished on a Buehler Metasery (Buehler, Lake Bluff, Ill., USA). Longitudinal sections of 5 thickness were cut using a Reichert-Jung RM 2165 microtome (Leica Microsystems, Jena, Germany) using a D-profile tungsten carbide knife, mounted on charged slides, and stained with either Goldner's trichrome or Toluidine Blue O (pH 3.7).

Statistical Analysis

Results were assessed using Student's t test to compare 2 groups or by 1-way ANOVA with Bonferroni post hoc test for comparisons between groups and expressed as means±SE. A value of $P<0.05$ was considered significant.

The results of the experiments are now described.

PEDF Inhibits Adipogenesis by Suppressing PPARγ and its Coactivator Peroxisome Proliferator-Activated Receptor γ Coactivator 1α (PGC1α)

Experiments were conducted to assess the ability of PEDF to modulate murine and hMSC differentiation into adipocytes. MSCs derived from stromovascular cells (SVCs) from adult wildtype and PEDF-knockout mice (KO) were able to differentiate into adipocytes by day 8 (FIG. 1A). PEDF (500 ng/ml) added on day 1 or day 3 significantly inhibited adipogenesis (FIG. 1B). This was accompanied by suppression of the proadipogenic transcription factors PPARγ, PGC1α, CCAAT/enhancer-binding protein-α (CEBPα), and the adipocyte marker ADIPOQ on day 1 (FIG. 1C) and day 3 (FIG. 1D). PPARγ suppression was greater when PEDF was started on day 1 compared with day 3. Even at this later time, PEDF inhibited PPARγ and PGC1α expression by nearly 50% in both WT and KO SVCs (FIG. 1D). PEDF similarly inhibited proadipogenic transcription factors in hMSCs (FIG. 1E). Thus, PEDF inhibits adipogenesis by inhibiting the key proadipogenic transcription factors, PPARγ and its coactivator PGC1α.

Figure 2:
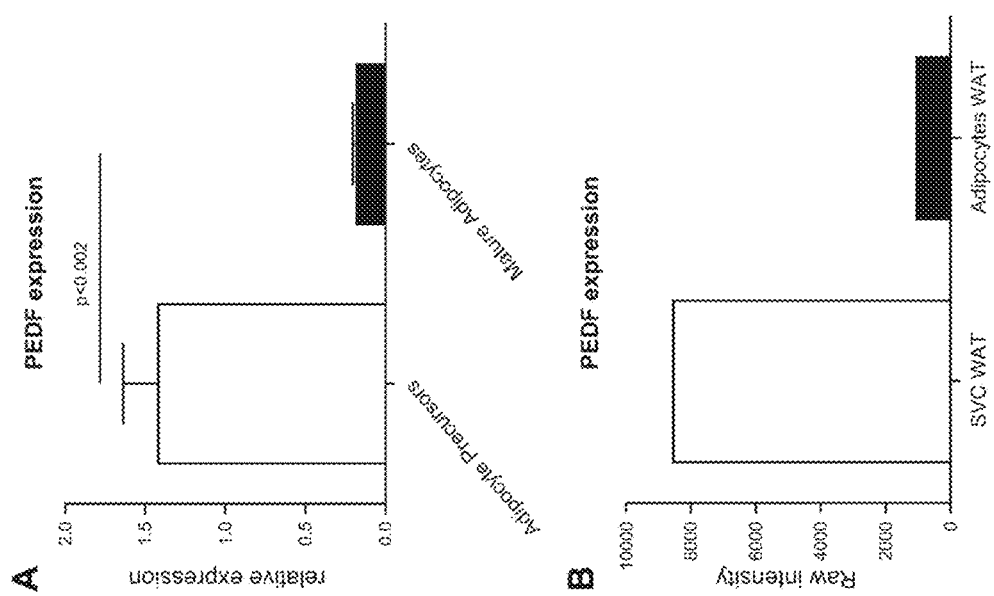
FIG. 2, comprising
Figure 7:
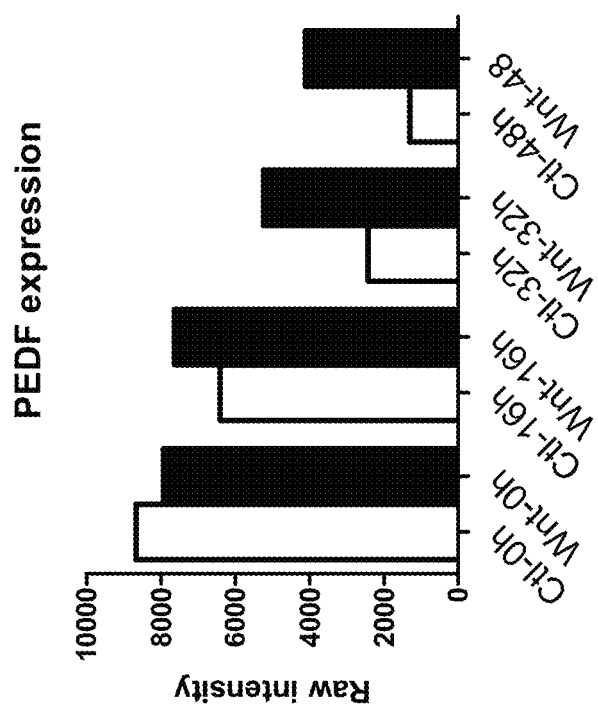
FIG. 7 is a graph depicting the results of example experiments demonstrating that preadipocytes expressing Wnt-1 maintained cells in an undifferentiated state despite the influence of pro-adipogenic media; Wnt-1 maintained PEDF expression compared to control non-Wnt secreting cells.

PEDF is Suppressed During Adipogenesis, and Wnt Expression Maintains PEDF Expression If PEDF were suppressed during adipogenesis, it would support its function as a negative regulator of adipocyte development. Data on PEDF expression by adipocyte precursors and adipocytes, however, are discordant. Some proteomic studies note high PEDF levels in preadipocytes that declined markedly early in adipogenesis, but others demonstrate high PEDF secretion by mature adipose tissue (Kratchmarova et al., 2002, Mol Cell Proteomics, 1: 213-222; Crowe et al., 2009, Cell Metab, 10:40-47). To clarify this issue, FACS-sorted adipocyte precursors (CD45$^-$, CD31$^-$, CD29$^+$, CD34$^+$, and Sca-1$^+$) were compared with mature adipocytes for PEDF expression (Rodeheffer et al., 2008, Cell, 135:240-249). Adipocyte progenitors had 8-fold higher PEDF levels compared with mature adipocytes (FIG. 2A). To evaluate these results in the context of previous analyses of adipogenesis, PEDF expression during adipogenesis was analyzed using unbiased microarray data (Ross et al., 2002, Mol Cell Biol., 22:5989-5999). PEDF expression was similarly reduced by nearly 90% in SVCs undergoing adipogenesis (FIG. 2B), analogous to the results seen in the present FACS-sorted study. Wnt agonists maintain preadipocytes in an undifferentiated state despite adipogenic stimuli (Ross et al., 2002, Mol Cell Biol., 22:5989-5999). Under Wnt expression and adipogenic medium, PEDF levels were maintained to a greater extent than those cells without Wnt stimulation (FIG. 7). FACS-sorted adipocyte precursors and unbiased microarray data demonstrate that PEDF expression is markedly suppressed to a similar extent after adipocyte differentiation. Wnt proteins, which inhibit adipogenesis, moreover, increase PEDF expression. These findings illustrate the ability of Wnt signaling to maintain antiadipogenic signals such as PEDF, which are suppressed during adipogenesis (Wang et al., 2009, Am J Physiol Endocrinol Metab, 297: E1378-1387; Kratchmarova et al., 2002, Mol Cell Proteomics, 1: 213-222).

PEDF Promotes Mineralization and Osteoblast Differentiation In Vitro

Figure 3:
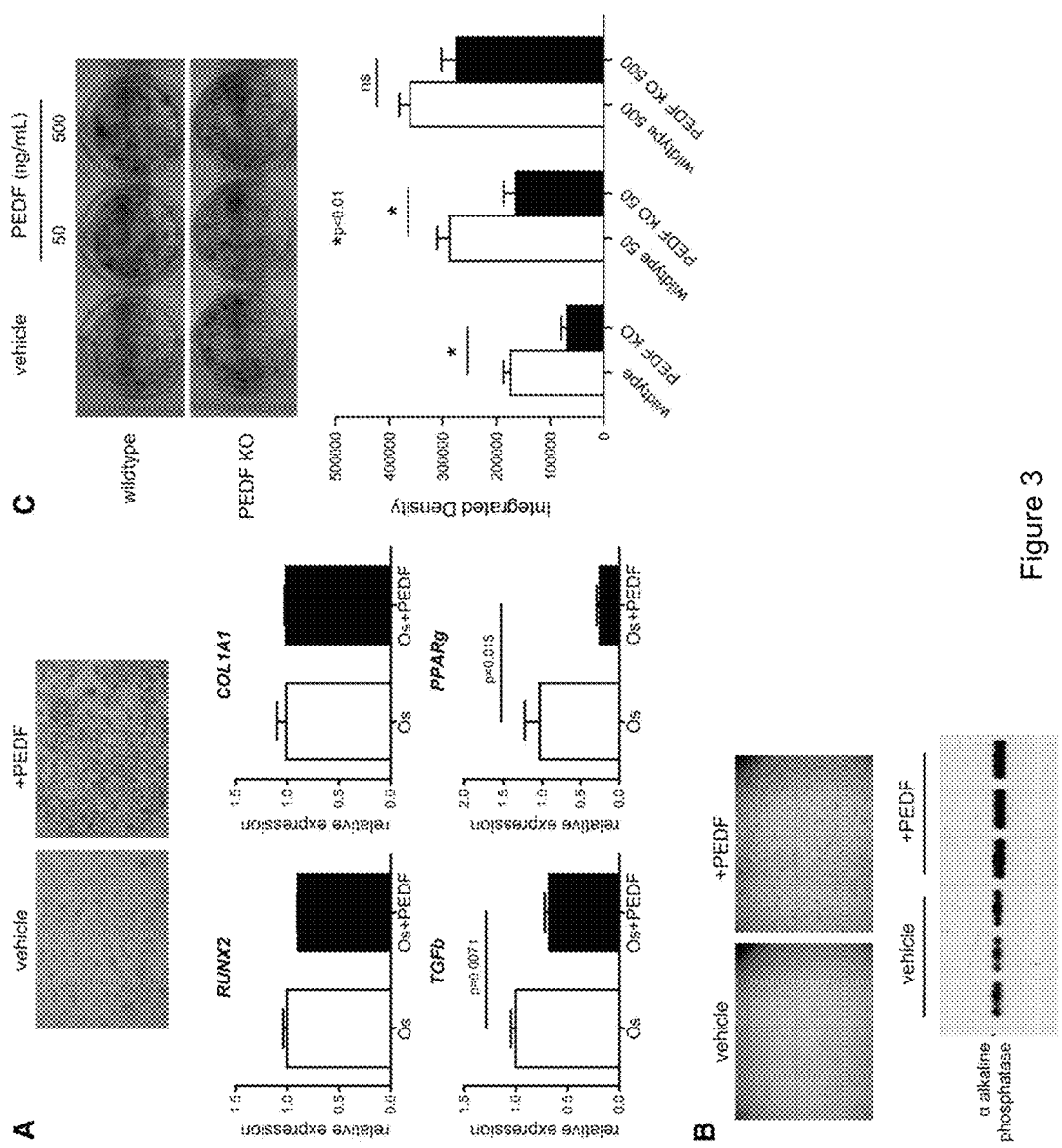
FIG. 3, comprising

To define the role of PEDF in osteoblast mineralization and differentiation, SVCs from PEDF KO mice, hMSCs, and osteoblast progenitors were induced to undergo osteoblast differentiation in the absence and presence of PEDF. Exogenous PEDF treatment for 21 days increased Alizarin Red staining of KO SVCs above that found in vehicle-treated cells (FIG. 3A). PEDF did not affect the prototypical bone transcription factors, Runx2 (FIG. 3A) or Sp7, at day 21 of differentiation. Collagen Ia expression was also not different in PEDF-treated cells consistent with results noted in clinical OI type VI where the absence of PEDF was not associated with collagen mutations or processing (Venturi et al., 2012, J Bone Miner Res., 27: 723-72). Comparable to the results seen in adipogenesis, PEDF markedly reduced PPARγ expression (FIG. 3A), a negative regulator of osteoblast differentiation, by nearly 80% (Leck-Czernik et al., 2002, Endocrinology, 143: 2376-2384). PEDF also reduced the expression of other negative regulators of bone formation, such as transforming growth factor β (TGF-β) (FIG. 3A) (Bailey et al., 2012, Biochem Biophys Res Commun, 422:488-493; Koli et al., 2008, Bone, 43: 679-688). Thus, PEDF promotes osteoblast differentiation by suppressing negative regulators of bone formation.

Figure 8:
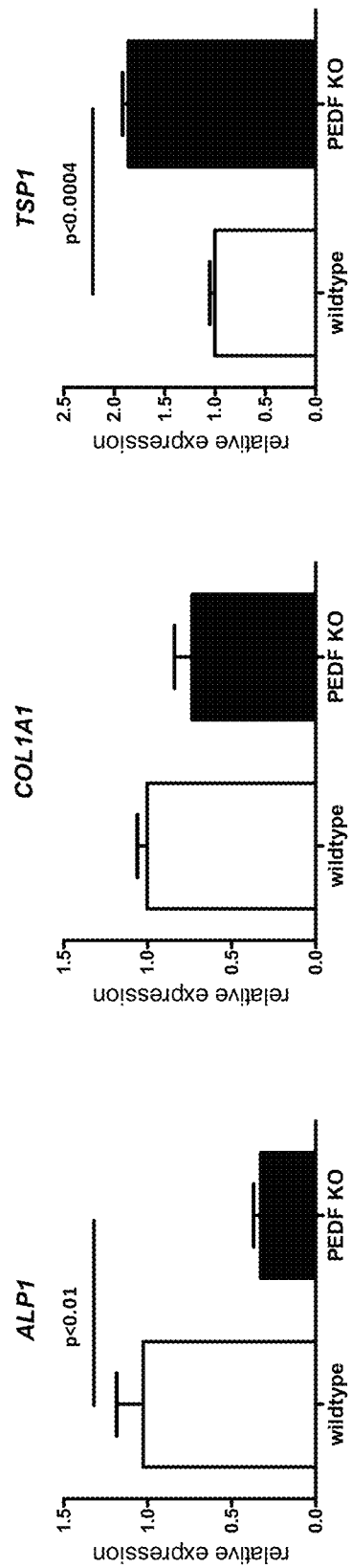
FIG. 8 are a set of graphs depicting the results of example experiments. Osteoblast progenitor cells 10 days after isolation from wildtype and KO calvaria demonstrate decreased alkaline phosphatase expression consistent with impaired osteoblast maturation. Increased thrombospondin-1, a negative regulator of osteoblast differentiation, was also increased in PEDF KO osteoblast progenitors. Collagen IA1 expression was not different between wildtype and KO progenitor cells.

It was next determined whether PEDF could differentiate hMSCs and osteoblast progenitors toward the osteoblast lineage. Adding PEDF to hMSCs increased alkaline phosphatase, a marker of osteoblast differentiation, by staining and protein levels (FIG. 3B). In committed osteoblast progenitors, PEDF KO cells demonstrated reduced alkaline phosphatase intensity compared with WT cells at baseline (FIG. 3C). Gene expression confirmed diminished alkaline phosphatase expression in PEDF KO compared with WT cells without differences in collagen 1A1 (FIG. 8). In addition, thrombospondin 1 (TSP-1), a negative regulator of late osteoblast maturation (Bailey et al., 2012, Biochem Biophys Res Commun, 422:488-493), was increased in KO cells (FIG. 8). Restoring PEDF (50 ng/ml) to KO osteoblast progenitors resulted in alkaline phosphatase intensity that was similar to untreated WT cells (FIG. 3C). With higher PEDF concentrations (500 ng/ml), alkaline phosphatase staining was similar between WT and PEDF KO cells (FIG. 3C). These results indicate that PEDF can induce osteoblast differentiation in SVCs, hMSCs, and committed osteoblast progenitors. Moreover, PEDF-mediated blockade of adipogenesis and promotion of osteogenesis were associated with marked PPARγ suppression, indicating a common pathway by which PEDF exerts differentiation of MSCs.

PEDF Acts as a Wnt Agonist in Early MSCs

Figure 4:
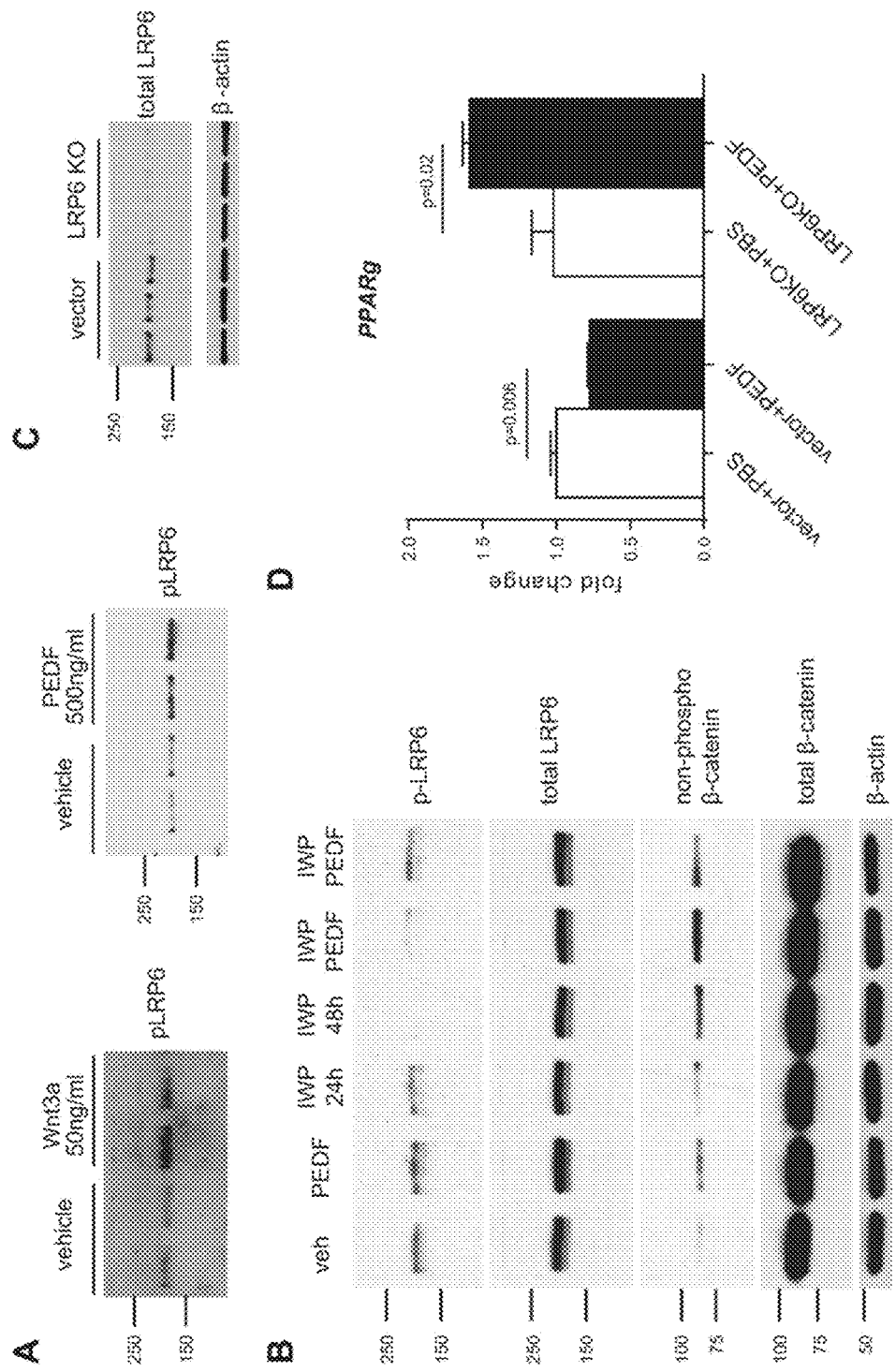
FIG. 4, comprising

Wnt-β-catenin signaling can determine osteoblast vs. adipocyte specification through suppression of transcription factors PPARγ and CEBPα (Krishnan et al., 2006, J. Clin. Invest., 116: 1202-1209; Leck-Czernik et al., 2002, Endocrinology, 143: 2376-2384; Ross et al., 2000, Science, 289:950-953). Since PEDF treatment resulted in a transcriptional profile akin to Wnt activation (FIG. 1C and FIG. 3A), experiments were conducted to interrogate the ability of PEDF to modulate canonical Wnt-β-catenin signaling including the activation (phosphorylation) status of the Wnt cell surface receptor LRP6 and the ratio of active (nonphosphorylated) β-catenin to total β-catenin. The prototypical agonist, Wnt3a, resulted in increased LRP6 phosphorylation of hMSCs (FIG. 4A). Similarly, PEDF treatment of hMSCs led to increased LRP6 phosphorylation (FIG. 4A). Since PEDF had functional effects that indicated it acts as a Wnt agonist but only minimal effects on active β-catenin levels under medium conditions where endogenous Wnt proteins would be present, it was assessed whether PEDF functions directly on LRP6 activation or acts indirectly by increasing endogenous Wnt production. To remove endogenous Wnt production, hMSCs were preincubated with the potent small molecule IWP-2 for 24-48 hours (Chen et al., 2009, Nat Chem Biol, 5: 100-107). IWP-2 incubation (48 h) alone effectively blocked endogenous Wnt production as evidenced by near absence of LRP6 phosphorylation (FIG. 4B). The addition of PEDF to IWP-2-treated cells led to LRP6 phosphorylation and enhanced levels of active β-catenin (FIG. 4B). Thus, PEDF functions as a direct Wnt agonist in early or new hMSCs.

It was next evaluated whether the suppressive effect of PEDF on PPARγ expression was LRP6 dependent. Knockdown of total LRP6 was confirmed in 3T3-L1 adipocyte precursors (FIG. 4C). In control (vector) cells, PEDF significantly inhibited PPARγ expression despite commitment of these cells to the adipocyte lineage (FIG. 4D). In contrast, PEDF induced PPARγ expression in cells with LRP6 knockdown (FIG. 4D), demonstrating that the suppressive actions of PEDF on PPARγ expression is LRP6 dependent.

Figure 5:
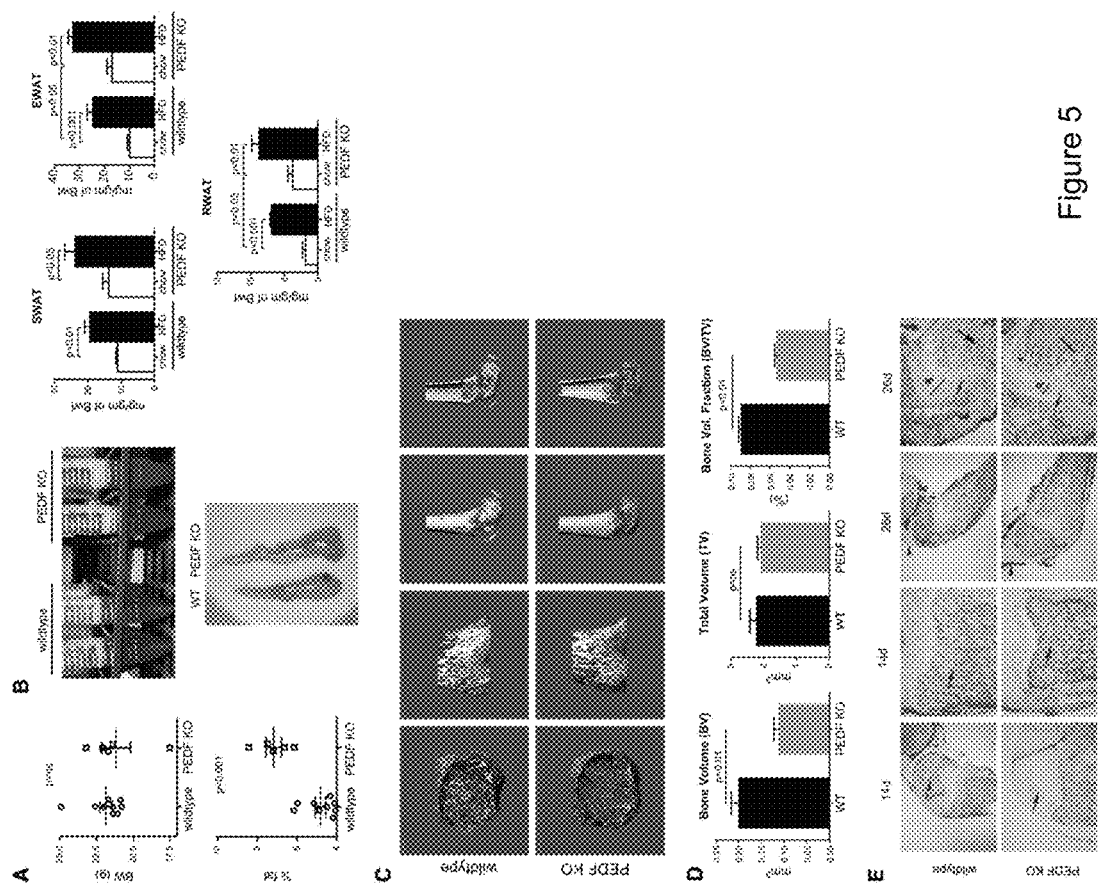
FIG. 5, comprising

PEDF Deficiency in Mice Results in Increased Total Body Fat and Altered Bone Mineralization Given human studies showing elevated circulating PEDF in the setting of obesity, it may have been predicted that PEDF KO mice would be lean. However, 12-wk-old PEDF KO mice exhibited a nearly 50% increase in total body adiposity as determined by MR spectroscopy but similar body weights (FIG. 5A). Dissection of subcutaneous, epididymal, and retroperitoneal fat pads in 12-wk-old mice confirmed increased adiposity with PEDF deficiency (FIG. 5B). Differences in fat depot size occurred under both normal and high fat diets (FIG. 5B). These findings indicate that absence of PEDF is permissive for increased adipogenesis in vivo, illustrating its systemic role as a negative regulator of adipogenesis.

Figure 9:
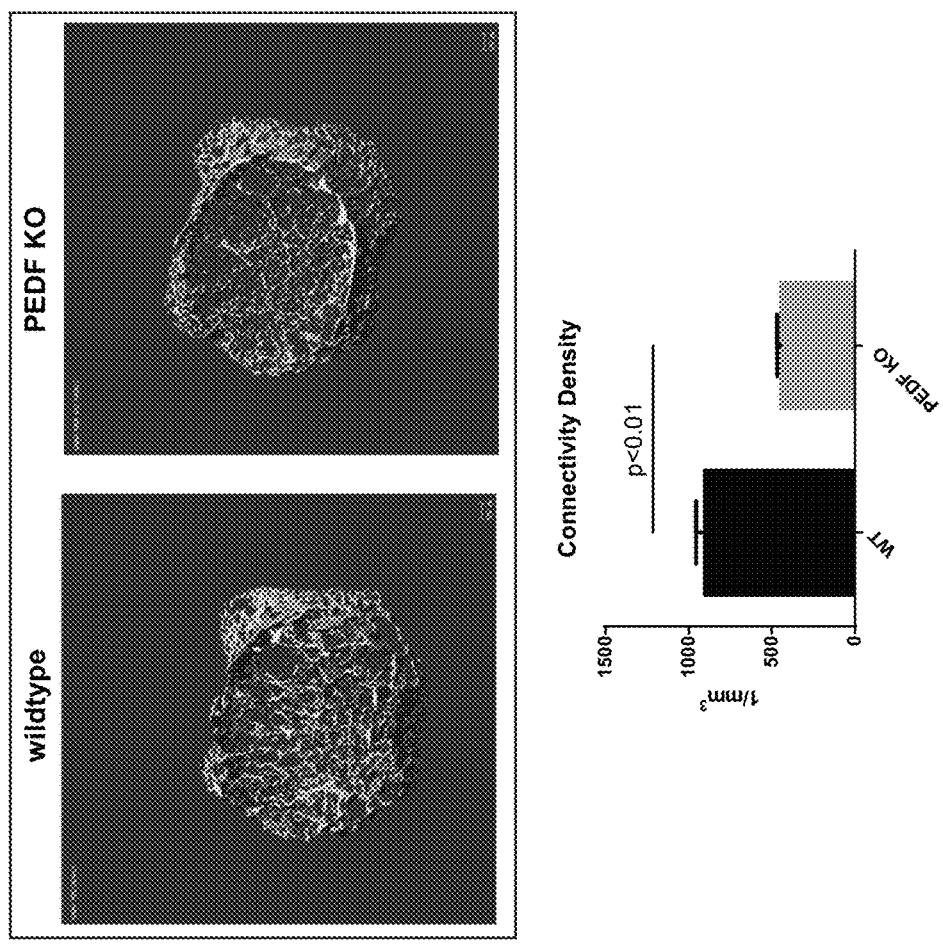
FIG. 9 depicts the results of example experiments. (top) Additional microCT-obtained images of trabecular bone morphology from wildtype and PEDF KO femurs show diminished trabecular bone mass. (bottom) The connectivity density, a measure of the extent of connections between trabeculae, was decreased by more than 50% in PEDF KO femurs.

To evaluate whether PEDF deficiency in mice recapitulates the PEDF null mutation seen in patients, bone volumes and mineralization were examined in femurs and tibiae at multiple time points. MicroCT analysis showed decreased trabecular bone volume along the distal femur (FIG. 5C; left panels, cross section of trabecular volume; left center panels, dorsal frontal view). Surface and cut images along the distal femur further illustrated the decrease in bone density in PEDF KO mice (FIG. 5C; right center panels, left lateral surface; right panels, cut left lateral view). Trabecular bone volume (BV) in PEDF KO mice (FIG. 5D) was >40% less than in control mice, while the total volume (TV) between groups was not different. Thus, the diminished bone volume fraction (BV/TV) in PEDF KO mice primarily reflected the loss of trabecular volume. The deficiency in the trabecular bone volume of KO mice was further evident in a diminished connectivity density (FIG. 9). Goldner's staining revealed decreased mineral content in the epiphysis and the chondro-osseous junction of 14-d-old mice (FIG. 5E, arrows). At 26 d, mineralization was evident in the epiphysis of PEDF KO mice, but the growth plate was smaller and less organized in PEDF KO mice compared with controls (FIG. 5E). Specifically, the zone of proliferating chondrocytes was diminished in PEDF KO mice (FIG. 5E). Thus, PEDF appears necessary for normal bone formation in mice, with PEDF deficiency recapitulating the defective bone volumes and hypomineralization seen in human OI type VI.

Role of PEDF in MSC Differentiation

Human diseases with distinct phenotypes reflecting the extremes of PEDF expression demonstrate the new role, described herein, for this factor in regulating MSC differentiation fate to adipocytes or osteoblasts. PEDF markedly inhibited the adipogenic drive of SVCs and hMSCs when given at the early phases of adipocyte differentiation. This effect coincided with suppression of the prototypical adipogenic transcription factors PPARγ and its coactivator PGC1α and is analogous to an antiadipocyte differentiation effect that was also confined to an early time point in 3T3-L1 preadipocytes (Wang et al., 2009, Am J Physiol Endocrinol Metab, 297: E1378-1387). In contrast, PEDF promoted osteoblast differentiation of MSCs and committed osteoblast progenitors. The functional effects of PEDF were accompanied by suppression of PPARγ and other inhibitors of osteoblast differentiation such as TGF-β and TSP-1 (Leck-Czernik et al., 2002, Endocrinology, 143: 2376-2384; Bailey et al., 2012, Biochem Biophys Res Commun, 422:488-493). Furthermore, it is demonstrated herein that PEDF functions as a Wnt agonist in hMSCs and that its suppressive action on PPARγ is LRP6 dependent, thereby linking canonical Wnt-β-catenin signaling with the ability of PEDF to suppress PPARγ.

Figure 6A:
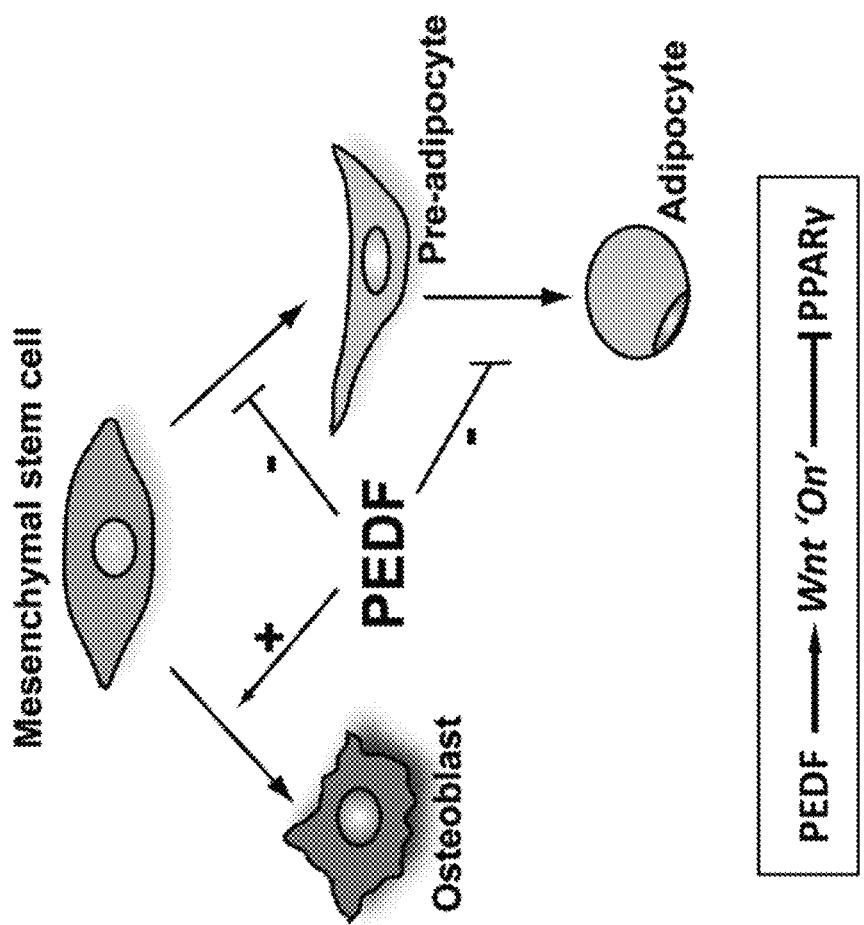
FIG. 6A and FIG. 6B, are a set of schematic illustrations depicting the role of PEDF in osteoblast differentiation.

Previous studies of the PEDF KO phenotype provided insights into a potential role involving MSC differentiation. The first study described abnormalities in the matricellular compartment with stromal expansion in the prostate and pancreas (Doll et al., 2003, Nat Med, 9: 774-780). In subsequent studies, activation of mesenchymal progenitor-derived cells was shown in the pancreas and livers in the absence of injury, with accentuated fibrotic responses on injury (Chung et al., 2009, Gastroenterology, 136:331-340 e332; Schmitz et al., 2011, Am J Pathol, 179: 2990-2999). Robust staining for TIP47, a lipid droplet marker, and the presence of increased stromal adiposity indicated an adipogenic drive in the mesenchymal cell population of organs that are typically devoid of adipocyte infiltration (Grippo et al., 2012, Gut, 61: 1454-1464). As described herein, a bone defect that captures key aspects of human OI type VI and increased total body adiposity in the absence of PEDF implicates its role in directing MSC fate toward osteoblasts and away from adipocytes (FIG. 6A).

Stimulation of LRP6 phosphorylation by PEDF is consistent with the known effects of Wnt signaling on promoting osteogenesis at the expense of adipogenesis (Krishnan et al., 2006, J. Clin. Invest., 116: 1202-1209; Ross et al., 2000, Science, 289:950-953). However, the ability of PEDF to act as an LRP6 agonist is in contrast to a previous study by Park et al. (Park et al., 2011, Mol Cell Biol, 31:3038-3051) that demonstrated that PEDF functions as a Wnt antagonist. However, their results were noted in nonpluripotent cells of the eye, where comprehensive studies showed PEDF avidly binds LRP6 and prevents β-catenin nuclear translocation (Park et al., 2011, Mol Cell Biol, 31:3038-3051). Previous microarray analysis examining the effects of Wnt expression on undifferentiated cells lends evidence to the notion that PEDF is involved in Wnt signaling (Ross et al., 2002, Mol Cell Biol., 22:5989-5999). Wnt expression and PEDF both impede adipogenesis that is temporally restricted to the undifferentiated state (Wang et al., 2009, Am J Physiol Endocrinol Metab, 297: E1378-1387, Ross et al., 2002, Mol Cell Biol., 22:5989-5999), with PEDF expression being Wnt dependent (FIG. 7). This suggests a positive feedback loop to prevent adipocyte differentiation. Thus, the developmental status of the target cell appears to be a critical factor in determining whether PEDF acts as a Wnt agonist vs. antagonist.

Figure 6B:
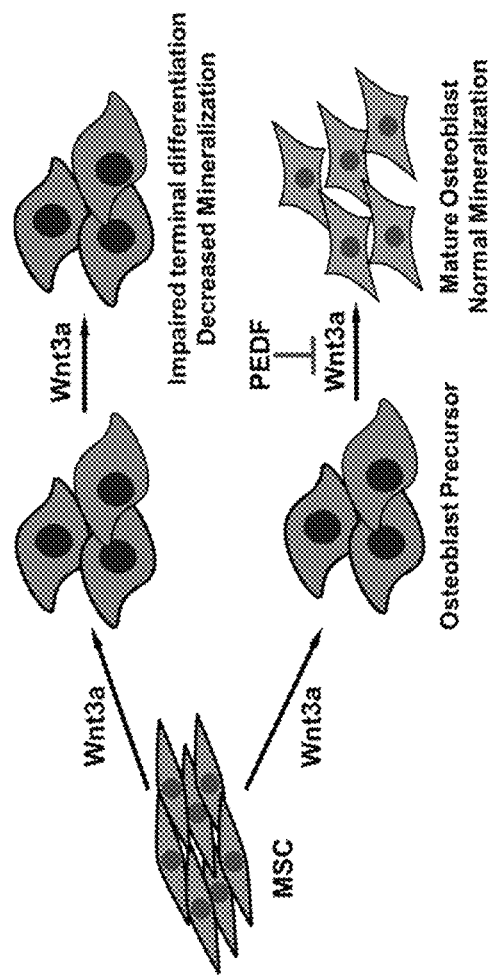

Further, the data indicates that in new hMSCs, PEDF acts as a Wnt agonist while in the later phases of osteoblast differentiation, PEDF is acting as an antagonist of Wnt activity. PEDF has biphasic effects on MSC to osteoblast differentiation. In early MSCs, PEDF serves as a redundant Wnt agonist. In the terminal phases of osteoblast differentiation, PEDF antagonizes Wnt3a mediated effects to induce terminal osteoblast differentiation (FIG. 6B). Wnt3a ligand directs mesenchymal stem cells (MSC) to the osteoblast lineage but unopposed Wnt3a impedes terminal osteoblast differentiation and normal mineralization. PEDF allows for osteoblast precursors to differentiate into mature osteoblasts through Wnt blockade.

The current results provide further evidence to implicate the role of PEDF in stem cell biology (Ramirez-Castillejo et al., 2006, Nat Neurosci, 9: 331-339; Doyon et al., 2009, J Biol Chem., 284: 25220-25229; Gonzalez et al., 2010, Proc Natl Acad Sci USA, 107:3552-3557). A proteomic screen of 806 secreted proteins found that PEDF was able to preserve hESC pluripotency without factors such as bFGF; implantation of PEDF-maintained hESCs developed into teratomas in vivo (Gonzalez et al., 2010, Proc Natl Acad Sci USA, 107:3552-3557). Knockdown of another proposed PEDF receptor, adipose triglyceride lipase (ATGL), in hESCs triggered the loss of Oct4 expression and led to cellular differentiation (Gonzalez et al., 2010, Proc Natl Acad Sci USA, 107:3552-3557). In the murine brain, PEDF secreted by cells of the subventricular zone were able to maintain neuronal stem cell renewal through activation of Notch signaling (Ramirez-Castillejo et al., 2006, Nat Neurosci, 9: 331-339). Moreover, in this and a prior study, it was shown that PEDF can negatively regulate TSP-1 levels (Schmitz et al., 2011, Am J Pathol, 179: 2990-2999). A recent study detailed that TSP-1 signaling suppresses c-Myc expression, thereby promoting cellular differentiation (Kaur et al., 2013, Sci Rep, 3:1673). The ability of PEDF to negatively regulate TSP-1 may therefore represent another mechanism by which PEDF modulates stem cell populations.

The reciprocal regulation of adipocyte vs. osteoblast differentiation by PEDF highlights the role of matricellular proteins in metabolic and bone homeostasis. For example, other matrix proteins such as secreted protein acidic and rich in cysteine (SPARC) can impede adipogenesis through activation of Wnt-β-catenin signaling, with SPARC-deficient animals displaying increased adipose mass and osteopenia (Bradshaw et al., 2003, Proc Natl Acad Sci USA, 100:6045-6050; Nie et al., 2009, J Biol Chem, 284:1279-1290). Similarly, PEDF contains binding sites for extracellular matrix constituents including collagen and heparin sulfate that likely play a role in its regulation and function (Yasui et al., 2003, Biochemistry, 42:3160-3167). The ability of PEDF to modulate Wnt-β-catenin signaling and suppress TSP-1 and TGF-β indicates a multifaceted regulation of MSC differentiation that likely involves regulation of other matricellular proteins.

Determining the degree of adiposity in those OI patients with the PEDF-null mutation would provide additional data to support the findings in the current study. A recent study comparing patients with OI type VI to patients with other OI subtypes (I, III, and IV) and healthy control subjects indicated that PEDF deficiency was significantly associated with increased body mass index (BMI) (Rauch et al., 2012, J Clin Endocrinol Metab, 97:E1550-E1556). The increased BMI in patients with OI type VI, the results of the current study, and the decreased body weights seen in PEDF-overexpressing mice support the notion that PEDF regulates body mass (Park et al., 2011, Mol Cell Biol, 31:3038-3051, Rauch et al., 2012, J Clin Endocrinol Metab, 97:E1550-E1556). These findings also suggest that elevated PEDF levels in the metabolic syndrome represent a homeostatic mechanism to coordinately modulate adipogenesis and ensure adequate bone mass (Sabater et al., 2010, J Clin Endocrinol Metab, 95: 4720-4728, Yamagishi et al., 2006, J Clin Endocrinol Metab, 91:2447-2450). Studies examining the metabolic phenotype of patients with OI type VI will likely shed new information on the role of in adipogenesis and metabolism.

The findings presented herein have additional clinical implications. For instance, the normal liver is a major source of circulating PEDF (Matsumoto et al., 2004, Hepatology, 40:252-259; Moreno-Navarrete et al., 2013, Int J Obes, doi: 10.1038/ijo.2012.223), and chronic liver diseases such as alcoholic steatosis and cirrhosis and primary biliary cirrhosis are characterized by a profound osteodystrophy. It has been previously demonstrated that chronic ethanol ingestion in two rodent models significantly depletes hepatic PEDF levels (Chung et al., 2009, Gastroenterology, 136:331-340 e332). Whether liver disease models that deplete hepatic PEDF lead to impaired osteoblast differentiation and a hepatic osteodystrophy-like phenotype is an area of investigation.

In summary, two human disease phenotypes associated with elevated or absent PEDF, the metabolic syndrome (increased adiposity) and OI type VI, are reflected in its ability to modulate MSC fate. The ability of PEDF to promote osteoblast differentiation suggests that elevated PEDF in the metabolic syndrome can be viewed as a regulatory mechanism to promote osteoblast differentiation in the setting of increasing body mass.

Example 2

In Vivo Effects of PEDF on Bone Mass

Figure 10:
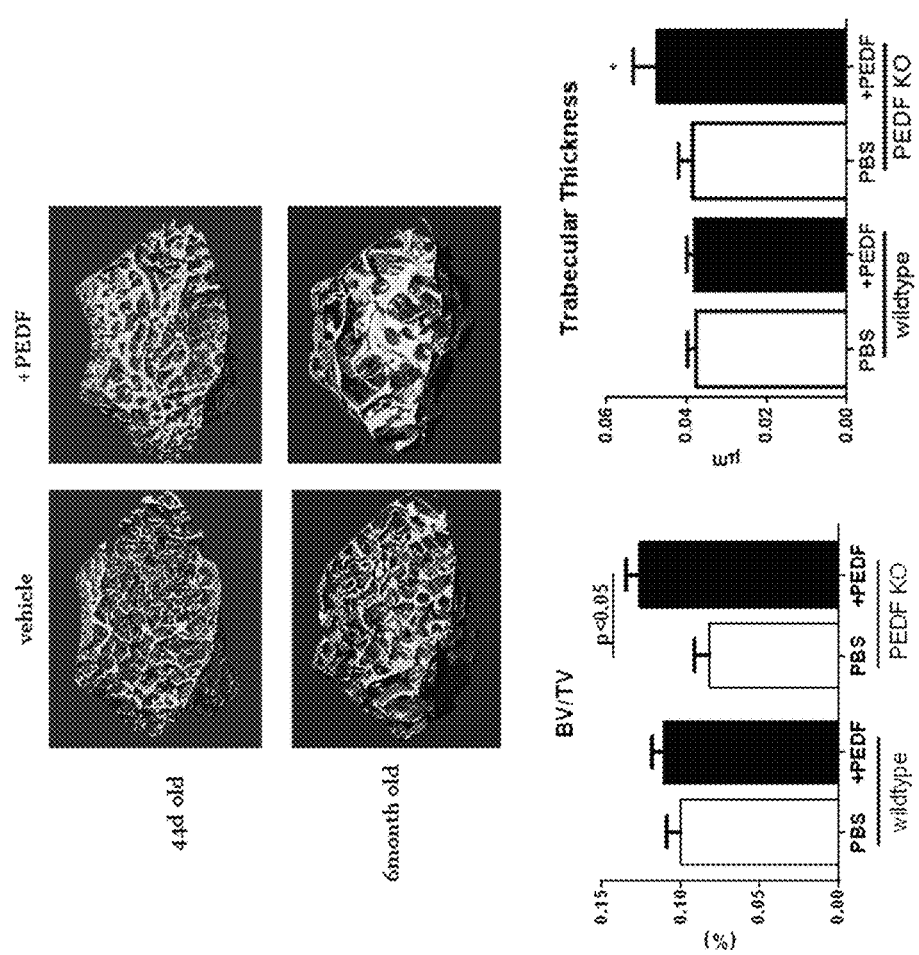
FIG. 10 depicts the results from example experiments demonstrating that PEDF increases trabecular bone volume (BV) and trabecular thickness in young (44 days) and old (6 months) PEDF KO mice. Graphs depict the results from old mice.

Experiments were conducted to examine the effects of PEDF treatment on bone in young (44 days) and old (6 month) PEDF knock-out mice. PEDF (200 ng) was delivered i.p. every third day for two weeks in young mice. In older mice, PEDF (25 µg/kg body weight) was injected ip every third day for 4 weeks. As shown in FIG. 10, recombinant PEDF increases trabecular bone volume (BV) and trabecular thickness in young and old PEDF KO mice.

Further in vivo experiments were conducted by delivering a one-time injection of PEDF (150 ng/gram body weight)-containing microspheres to young 19-day old mice. Full-length recombinant human PEDF was generated in HEK cells. PEDF integrity was confirmed by SimplyBlue staining (Invitrogen), and then dialyzed in PBS. PEDF-containing microspheres were prepared as described. Briefly, sterile alginate (2%) and HPMC (0.2%) were dissolved in ultrapure $H_2O$, followed by the direct dissolution of PEDF for a theoretical maximum of 0.2 µg PEDF/mg alginate. Isooctane+5% (v/v) Span 80 was homogenized at 17,500 rpm, and the alginate/HPMC/PEDF solution was added dropwise. Then, 30% (v/v) aqueous Tween 80 was added dropwise, and the emulsion was mixed for 3 minutes. An aqueous solution of calcium chloride (100 mM) was added at a rate of 4 ml/min. After mixing, 2-propanol was added and the particles were allowed to cure for 3 minutes. The particles and supernatant were centrifuged at 4000 rpm for one minute. The supernatant was then removed and particles were washed twice in 2-propanol and air-dried. Particles were resuspended in ultrapure $H_2O$ and lyophilized. PEDF loading was analyzed with the microBCA assay (Thermo Scientific) according to the manufacturer's protocol. Intraperitoneal injections were given 19-day old male mice with a one-time injection of PEDF-containing or vehicle-containing microspheres (PEDF 150 ng/gm body weight, n=9/group) and bones collected after three weeks.

Figure 11:
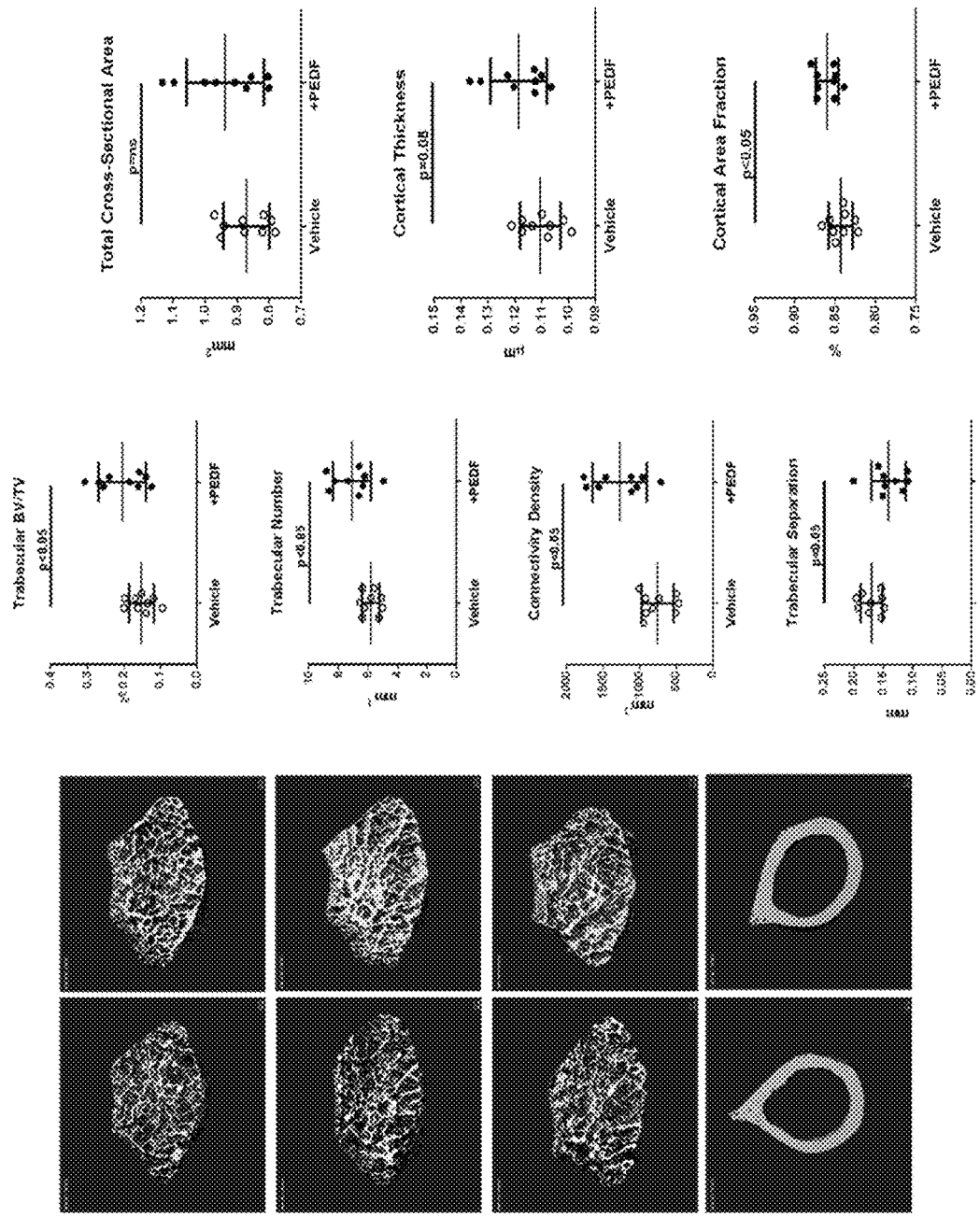
FIG. 11 depicts the results from example experiments demonstrating that a one-time injection of PEDF (150 ng/gram body weight)-containing microspheres increases bone volumes in young 19-day-old mice treated at three weeks post injection. (left) Representative μCT images of femurs from vehicle and PEDF-treated mice. (middle) Increased bone volume fraction (BV/TV), trabecular number, connectivity density, and decreased separation after PEDF treatment. (right) Total cross-sectional area of the cortical bone was not different between the groups but the cortical area fraction was significantly higher in PEDF-treated mice, reflecting a trend toward greater cortical thickness. Values expressed as mean±SD. n=9 mice/group.

Bone volume in the treated mice was analyzed three weeks after injection. As shown in FIG. 11, the one-time injection of PEDF-containing microspheres increases bone volumes in the PEDF-treated mice at 3 weeks post-injection, as compared to vehicle-treated mice. For example, PEDF treatment resulted in increased bone volume fraction (BV/TV), trabecular number, connectivity density, and decreased separation (FIG. 11, middle). Total cross-sectional area of the cortical bone was not different between the groups but the cortical area fraction was significantly higher in PEDF-treated mice, reflecting a trend toward greater cortical thickness (FIG. 11, right).

Figure 12:
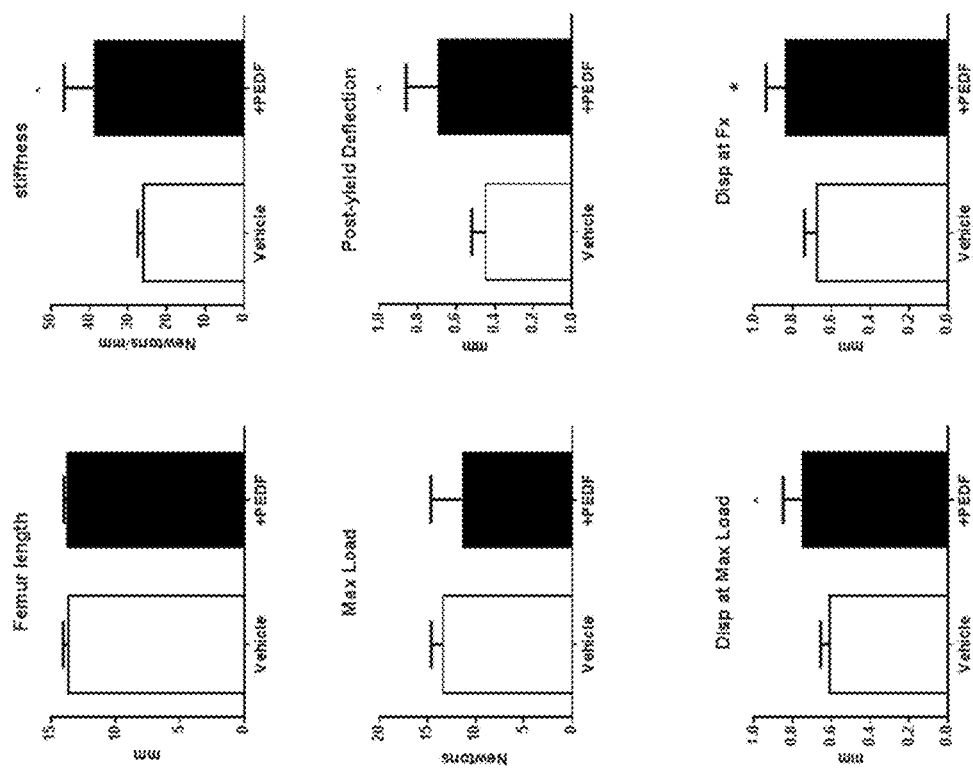
FIG. 12 depicts the results from example experiments where Biomechanical testing of vehicle and PEDF treated bones demonstrates that PEDF restoration enhances the flexibility of femurs in PEDF KO mice. Femur length was not different between vehicle or PEDF-treated groups. PEDF increased bone stiffness, the slope of the load applied to the bone vs displacement of bone. Maximum load was not different in PEDF-treated mice. The deformation of bone after the yield point, a measure of bone ductility increased after PEDF treatment. Displacement of femurs at maximum load and at fracture (Fx) point increased after PEDF treatment, indicating bones that are less brittle with force applied. *=$p<0.05$ by Student's t-test. Values expressed as mean±SD.

Further experiments were done to compare the biomechanical properties of PEDF-treated and vehicle-treated bones. Biomechanical testing of vehicle and PEDF treated bones demonstrated that PEDF restoration enhances the flexibility of femurs in PEDF KO mice (FIG. 12). Femur length was not different between vehicle or PEDF-treated groups. PEDF increased bone stiffness, the slope of the load applied to the bone vs displacement of bone. Maximum load was not different in PEDF-treated mice. The deformation of bone after the yield point, a measure of bone ductility increased after PEDF treatment. Displacement of femurs at maximum load and at fracture (Fx) point increased after PEDF treatment, indicating bones that are less brittle with force applied.

Example 3

PEDF Peptide Mimetics

Figure 13:
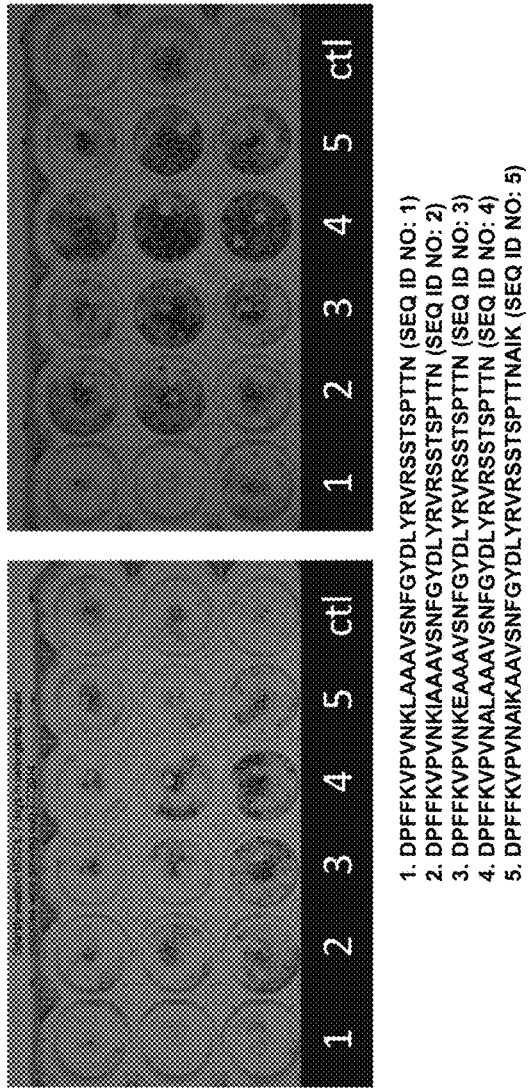
FIG. 13 depicts the results from example experiments demonstrating that PEDF-derived peptides induce human MSCs to proliferate in vitro. The cell staining demonstrate induction of cellular number in response to the peptides.
Figure 13:
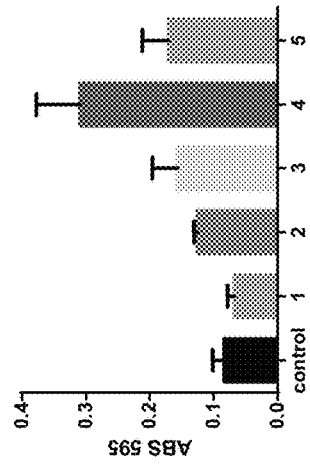

Experiments were conducted to examine the effects of various PEDF-derived peptides on MSC differentiation. The amino acid sequences of the five peptides that were examined were as follows:

```
                                     (SEQ ID NO: 1)
DPFFKVPVNKLAAAVSNFGYDLYRVRSSTSPTTN (SEQ ID NO: 2)
DPFFKVPVNKIAAAVSNFGYDLYRVRSSTSPTTN (SEQ ID NO: 3)
DPFFKVPVNKEAAAVSNFGYDLYRVRSSTSPTTN (SEQ ID NO: 4)
DPFFKVPVNALAAAVSNFGYDLYRVRSSTSPTTN (SEQ ID NO: 5)
DPFFKVPVNAIKAAVSNFGYDLYRVRSSTSPTTNAIK.
``` hMSCs were cultured for 7 days in osteogenic media with or without the peptide (100 nm) on non-culture treated plates. As shown in FIG. 13, it was observed that PEDF-derived peptides induce human MSCs to proliferate. After the 7 days of culture, the proliferated cells are likely osteoblast progenitor cells.

Figure 14:
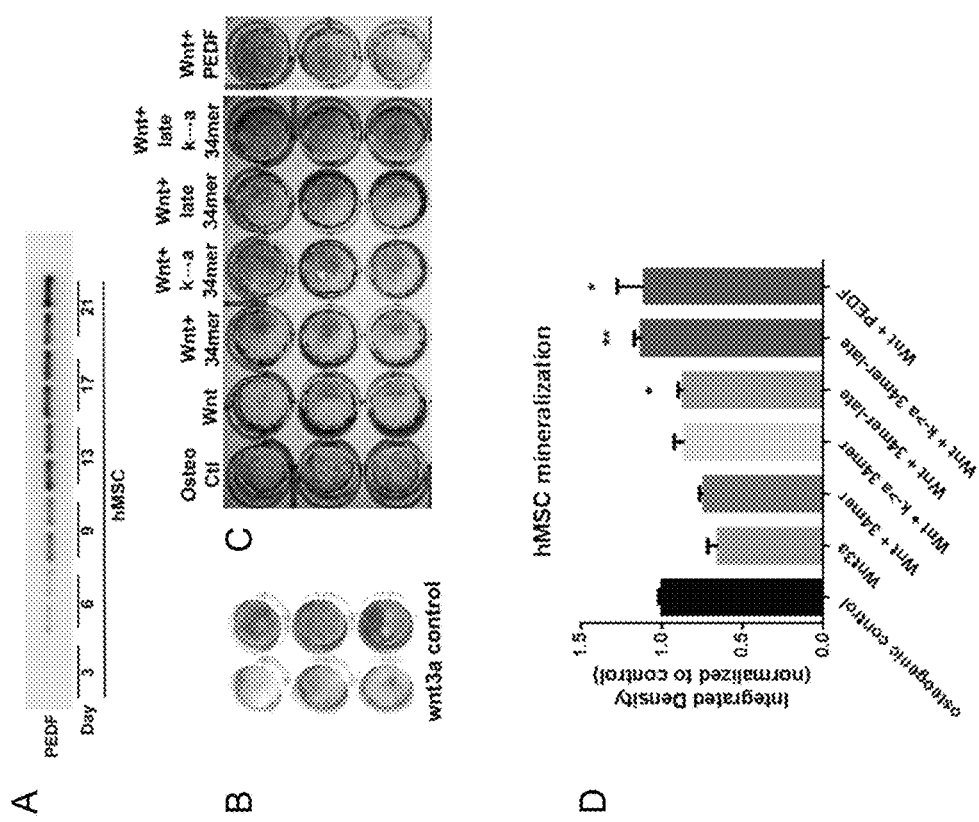
FIG. 14, comprising

Experiments were conducted to evaluate the effect of PEDF-derived peptides on the mineralization of hMSCs. The endogenously secreted amount of PDF from hMSCs over 21 days in culture in osteogenic media is shown in FIG. 14A. Alizarin red staining of 21-day-old hMSC cultures with continuous Wnt3a (50 ng/ml) exposure versus controls demonstrates that continuous and unopposed Wnt3a leads to diminished mineralization (FIG. 14B). hMSC cultures were treated with continuous Wnt3a 50 ng/ml alone or in combination with PEDF 34-mer (100 nM) (SEQ ID NO: 1), or mutated K→A peptide (SEQ ID NO: 4). For "late" groups, PEDF 34-mer was added only during the last 8 days of the differentiation protocol. Mineralization was assessed by Alizarin red staining (FIG. 14C). Quantitation of Alizarin red staining demonstrates gain of function properties with K→A mutated PEDF 34-mer over the native PEDF and that addition of this mutated peptide in the last eight days of differentiation provides osteoblast mineralization comparable to the full-length protein added for 21 days (FIG. 14D). This data demonstrates that SEQ ID NO: 4 added in the final phase (last 8 of 21 days) stimulates mineralization of human MSCs (hMSCs).

Figure 15:
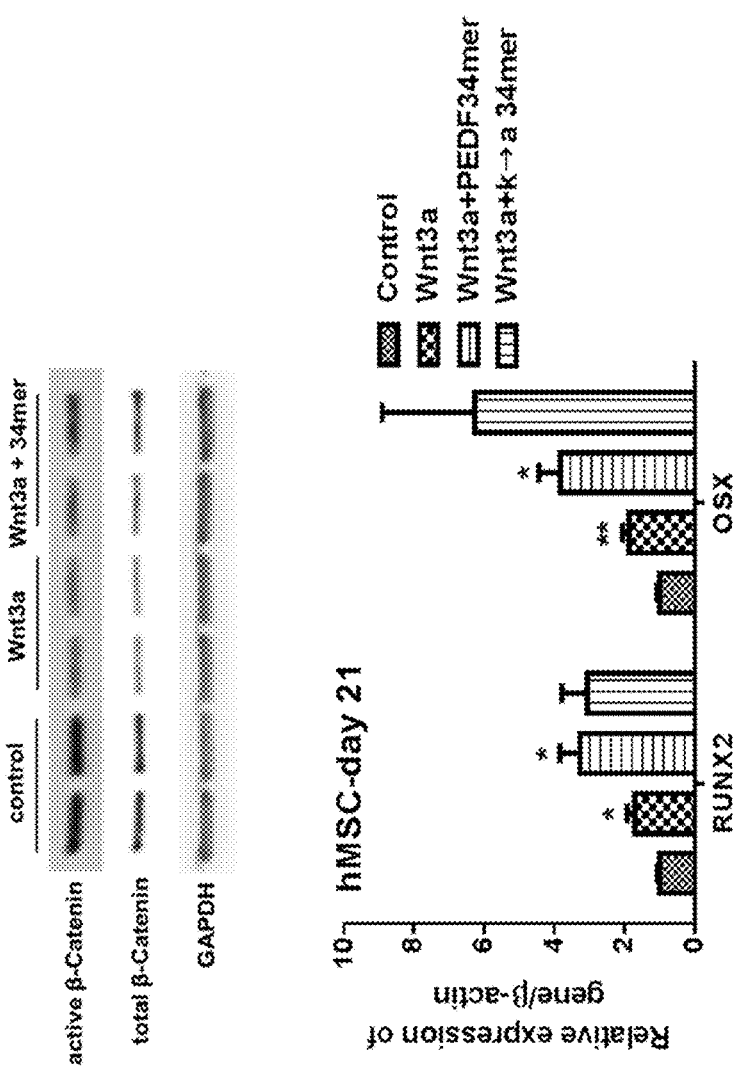
FIG. 15 depicts the results of example experiments demonstrate that unopposed and continuous Wnt3a exposure suppresses active β-catenin, a transcriptional regulator of osteoblast differentiation. Co-administration of PEDF with Wnt3a increases active β-catenin and bone lineage markers. (top) PEDF 34-mer peptide with Wnt3a increases the levels of active β-catenin. (bottom) Expression levels of genes that characterize mature osteoblasts from hMSC differentiated for 21 days shows that PEDF K→A 34 mer (SEQ ID NO: 4) increases the expression of osterix (OSX), a specific marker of a mature osteoblast. Cultures incubated in 50 ng/ml Wnt3a and 100 nM PEDF peptides as indicated. *$p<0.05$, **$p<0.01$.

Experiments were conducted to evaluate the effect of Wnt3a and PEDF-derived peptides on β-catenin, a transcriptional regulator of osteoblast differentiation. Cultures incubated in 50 ng/ml Wnt3a alone or in combination with 100 nM PEDF-derived peptides. As shown in FIG. 15, PEDF 34-mer peptide with Wnt3a increases the levels of active β-catenin (FIG. 15, top). Together, this data demonstrates that unopposed and continuous Wnt3a exposure suppresses active β-catenin, a transcriptional regulator of osteoblast differentiation, and that co-administration of PEDF with Wnt3a increases active β-catenin and bone lineage markers. Expression levels of genes that characterize mature osteoblasts from hMSC differentiated for 21 days shows that PEDF K→A 34 mer (SEQ ID NO: 4) increases the expression of osterix (OSX), a specific marker of a mature osteoblast (FIG. 15, bottom).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for differentiating a stem cell into the osteoblast lineage, wherein the composition comprises:
an agent that increases PEDF activity, wherein the agent comprises an agent selected from the group consisting of:
 (a) a peptide comprising the amino acid sequence of SEQ ID NO: 4; and
 (b) an isolated nucleic acid encoding the amino acid sequence of SEQ ID NO: 4.

2. A method comprising culturing a stem cell in the presence of a composition comprising an agent that increases PEDF activity wherein the agent comprises an agent selected from the group consisting of:
 (a) a peptide comprising the amino acid sequence of SEQ ID NO: 4; and
 (b) an isolated nucleic acid encoding the amino acid sequence of SEQ ID NO: 4;
thereby differentiating the stem cell into the osteoblast lineage and generating a population of osteoblasts.

3. A method of treating or preventing a condition associated with reduced bone mass in a subject in need thereof, the method comprising administering to the subject an effective amount of a composition comprising an agent that increases PEDF activity, wherein the agent comprises an agent selected from the group consisting of:
 (a) a peptide comprising the amino acid sequence of SEQ ID NO: 4; and
 (b) an isolated nucleic acid encoding the peptide comprising the amino acid sequence of SEQID NO: 4.

4. The method of claim 3, wherein the condition is selected from the group consisting of osteogenesis imperfecta, osteoporosis, osteoarthritis, bone fracture, and cancer of the bone.

5. The method of claim 2, further comprising transplanting the population of osteoblasts to a subject, thereby treating or preventing a condition associated with reduced bone mass in the subject.

* * * * *